United States Patent
Weser et al.

(10) Patent No.: US 12,201,712 B2
(45) Date of Patent: Jan. 21, 2025

(54) METHOD FOR DYEING KERATINOUS MATERIAL, COMPRISING THE USE OF AN ORGANOSILICON COMPOUND, A PHOSPHORIC ACID ESTER AND A DYEING COMPOUND

(71) Applicant: Henkel AG & Co. KGaA, Duesseldorf (DE)

(72) Inventors: Gabriele Weser, Essen (DE); Ulrike Schumacher, Duesseldorf (DE); Caroline Kriener, Duesseldorf (DE); Jing Hodes, Hagen (DE); Claudia Kolonko, Remscheid (DE); Phillip Jaiser, Langenfeld (DE); Marc Nowottny, Moenchengladbach (DE); Juergen Schoepgens, Schwalmtal (DE); Carsten Mathiaszyk, Essen (DE); Torsten Lechner, Langenfeld (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 19 days.

(21) Appl. No.: 18/005,837

(22) PCT Filed: May 27, 2021

(86) PCT No.: PCT/EP2021/064187
§ 371 (c)(1),
(2) Date: Jan. 17, 2023

(87) PCT Pub. No.: WO2022/012808
PCT Pub. Date: Jan. 20, 2022

(65) Prior Publication Data
US 2023/0270652 A1 Aug. 31, 2023

(30) Foreign Application Priority Data
Jul. 17, 2020 (DE) .......................... 102020208951.5

(51) Int. Cl.
*A61Q 5/10* (2006.01)
*A61K 8/55* (2006.01)
*A61Q 5/06* (2006.01)

(52) U.S. Cl.
CPC .............. *A61K 8/556* (2013.01); *A61Q 5/065* (2013.01); *A61K 2800/43* (2013.01); *A61K 2800/87* (2013.01); *A61K 2800/884* (2013.01)

(58) Field of Classification Search
CPC ................ A61K 8/556; A61K 2800/43; A61K 2800/87; A61K 2800/884; A61K 8/55; A61K 8/585; A61Q 5/065
USPC ........................................................... 8/405
See application file for complete search history.

(56) References Cited

U.S. PATENT DOCUMENTS

| | | | |
|---|---|---|---|
| 2010/0083446 A1* | 4/2010 | Brun | A61K 8/891 8/405 |
| 2012/0183483 A1* | 7/2012 | Misu | A61K 8/39 8/408 |
| 2012/0325241 A1 | 12/2012 | Hashimoto et al. | |
| 2012/0325248 A1 | 12/2012 | Tan et al. | |
| 2015/0080338 A1* | 3/2015 | Lorant | A61K 8/8152 514/63 |
| 2017/0258695 A1 | 9/2017 | Consoli et al. | |

FOREIGN PATENT DOCUMENTS

| | | | | |
|---|---|---|---|---|
| EP | 2168633 A2 | 3/2010 | | |
| WO | WO 2011024300 A1 * | 3/2011 | ............... | A61Q 5/10 |
| WO | 2020088813 A1 | 5/2020 | | |

OTHER PUBLICATIONS

Laboratorios Lissia, Database GNPD [Online] Mintel; Mar. 26, 2018 (Mar. 26, 2018), Anonymous: Semi Permanent Hair Dye Cream, XP055841970, Database accession No. 5509583.

* cited by examiner

*Primary Examiner* — Eisa B Elhilo
(74) *Attorney, Agent, or Firm* — Lorenz & Kopf, LLP

(57) ABSTRACT

The subject of the present disclosure is a process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms, and
(a2) at least one phosphoric acid ester,
application of an agent (b) to the keratinous material, wherein the agent (b) comprises:
(b1) at least one sealing reagent,
wherein at least one of the agents (a) and (b) further comprises at least one colorant compound selected from the group of pigments and/or direct dyes.

18 Claims, No Drawings

METHOD FOR DYEING KERATINOUS MATERIAL, COMPRISING THE USE OF AN ORGANOSILICON COMPOUND, A PHOSPHORIC ACID ESTER AND A DYEING COMPOUND

CROSS-REFERENCE TO RELATED APPLICATION

This application is a U.S. National-Stage entry under 35 U.S.C. § 371 based on International Application No. PCT/EP2021/064187, filed May 27, 2021, which was published under PCT Article 21(2) and which claims priority to German Application No. 102020208951.5, filed Jul. 17, 2020, which are all hereby incorporated in their entirety by reference.

TECHNICAL FIELD

The subject of the present application is a method for treating keratinous material, in particular human hair, which comprises the application of two agents (a) and (b). The agent (a) is exemplified by its content of at least one organic silicon compound (a1) and at least one phosphoric acid ester (a2). The agent (b) comprises at least one sealing reagent (b1). Furthermore, either agent (a) or agent (b) or both agents (a) and (b) contain at least one colorant compound selected from the group of pigments and/or direct dyes.

A further subject of this application is a multi-component packaging unit (kit-of-parts) for dyeing keratinous material, in particular human hair, which comprises separately prepared at least three agent (a'), (a") and (b). Agents (a') and (a") can be used to prepare the agent (a) used in the process described above.

BACKGROUND

Also, a further subject of this application is a multi-component packaging unit (kit-of-parts) for dyeing keratinous material, in particular human hair, which comprises separately prepared at least five agents (a'), (a"), (b') and (b"). From agents (a') and (a"), the agent (a) used in the process described above can be prepared, and from agents (b') and (b"), the agent (b) used in the process described above can be prepared.

The change in shape and color of keratin fibers, especially hair, is a key area of modern cosmetics. To change the hair color, the expert knows various coloring systems depending on coloring requirements. Oxidation dyes are usually used for permanent, intensive dyeing with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyes with direct colorings usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed without residue by a few washes with surfactant-comprising cleaning agents. Various products of this type are available on the market under the name hair mascara.

If the user wants particularly long-lasting dyeing, the use of oxidative dyes has so far been his/her only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. The paper teaches that when the combination of a pigment, an organic silicon compound, a film-forming polymer and a solvent is used on hair, it is possible to produce colorations that are particularly resistant to abrasion and/or shampooing.

The great advantage of the organic silicon compound-based dyeing principle is that the high reactivity of this class of compounds enables fast coating. This means that extremely good coloring results can be achieved after short application periods of just a few minutes.

Mixtures of colorant compounds are often used in the coloring of keratinous materials, especially human hair. To avoid inegalities during dyeing, the infiltration behavior of the different colorant compounds should not be too dissimilar. In addition, the colorant compound pick-up behavior depends on numerous influencing factors, such as the state of the colorant compound in the agent (dissolved, aggregated, dispersed), local concentrations in the agent, etc.

There is a need to provide hair dyes with pigments that on the one hand have high wash and rub fastness and on the other hand give intense and homogeneous colorations.

BRIEF SUMMARY

Processes and kits-of-parts for dyeing keratinous material are provided herein. In an embodiment, a process for dyeing keratinous material includes the following steps:
  applying an agent (a) to the keratinous material, wherein the agent (a) comprises:
    (a1) at least one organic silicon compound selected from the group of silanes having one, two or three silicon atoms, and
    (a2) at least one phosphoric acid ester,
  applying an agent (b) to the keratinous material, wherein the agent (b) comprises:
    (b1) at least one sealing reagent.
  At least one of the agents (a) and (b) further comprises at least one colorant compound selected from the group of pigments and/or direct dyes.

In another embodiment, a kit-of-parts for dyeing keratinous material includes, separately packaged,
  a first container including an agent (a'), wherein the agent (a') comprises:
    (a1) at least one organic silicon compound selected from the group of silanes having one, two or three silicon atoms, and
  a second container including an agent (a"), the agent (a") comprising:
    (a2) at least one phosphoric acid ester,
  a third container including an agent (b), wherein the agent (b) comprises:
    (b1) at least one sealing reagent.
  At least one of the agents (a") and (b) further comprises at least one colorant compound selected from the group of pigments and/or direct dyes.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description. It is to be appreciated that all values as provided herein, save for the actual examples, are approximate values with endpoints or particular values intended to be read as "about" or "approximately" the value as recited.

Surprisingly, it has now been found that the task can be excellently solved if keratinous materials, in particular human hair, are colored by a process in which at least two agents (a) and (b) are applied to the keratinous materials (hair). Here, the first agent (a) comprises at least one organic silicon compound from the group of silanes with one, two or three silicon atoms and at least one phosphoric acid ester (a2). The second agent (b) comprises at least one sealing reagent (b1).

When the two agents (a) and (b) were used in a dyeing process, it was surprisingly possible to produce dyeing with particularly high uniformity, rub fastness and wash fastness.

A first object of the present disclosure is a method for coloring keratinous material, in particular human hair, comprising the following steps:

Application of an agent (a) to the keratinous material, wherein the agent (a) comprises:
- (a1) at least one organic silicon compound selected from the group of silanes having one, two or three silicon atoms, and
- (a2) at least one phosphoric acid ester, Application of an agent (b) to the keratinous material, wherein the agent (b) comprises:
- (b1) at least one sealing reagent, wherein at least one of the agents (a) and (b) further comprises at least one colorant compound selected from the group of pigments and/or direct dyes.

In the work leading to the present disclosure, it has been found that the preferential successive application of agents (a) and (b) enables the production of very stable and washfast colorations on the keratinous materials. Without being limited to this theory, it is suspected in this context that the joint application of organic silicon compound (a1) and phosphoric acid ester (a2) leads to the formation of a particularly resistant film on the keratinous material. Application of the second agent (b) seals the film applied to the keratinous material, making it more resistant to washing and/or abrasion. By using at least one colorant compound selected from the group of pigments and/or direct dyes in at least one of the agents (a) and (b), colored films can be obtained.

In this way, the colorant compounds can be permanently fixed to the keratinous material, so that extremely washfast colorations with good resistance to abrasion and/or shampooing could be obtained.

With the aid of the phosphoric acid ester (a2) uniform and intense colorations could also be obtained.

Keratinous Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.
Agents (a) and (b)

In the process described agents (a) and (b) are applied to the keratinous material, in particular human hair. The two agents (a) and (b) are different from each other.

In other words, a first object of the present disclosure is a method for treating keratinous material, in particular human hair, comprising the following steps:

Application of an agent (a) to the keratinous material, wherein the agent (a) comprises:
- (a1) at least one organic silicon compound selected from the group of silanes having one, two or three silicon atoms, and
- (a2) at least one phosphoric acid ester, and Application of an agent (b) to the keratinous material, wherein the agent (b) comprises:
- (b1) at least one sealing reagent, wherein at least one of the agents (a) and (b) further comprises at least one colorant compound selected from the group of pigments and/or direct dyes.

Agent (a)

The agent (a) comprises the ingredients (a1) and (a2) essential to the present disclosure.

The agent (a) may contain the two ingredients (a1) and (a2) in a cosmetic carrier, particularly preferably in an aqueous cosmetic carrier. This cosmetic carrier can be liquid, gel, or cream. Pasty, solid or powdery cosmetic carriers can also be used for the preparation of agent (a). For hair treatment, in particular hair coloring, such carriers are, for example, creams, emulsions, gels, or also surfactant-comprising foaming solutions, such as shampoos, foam aerosols, foam formulations or other preparations suitable for application to the hair.

Preferably, the cosmetic carrier comprises—based on its weight—at least 2 wt. % of water. Further preferably, the water content is above 10 wt. %, still further preferably above 20 wt. % and particularly preferably above 40 wt. %.

Organic Silicon Compounds from the Group of Silanes (a1)

As an ingredient (a1) essential to the present disclosure, the agent (a) comprises at least one organic silicon compound from the group of silanes having one, two or three silicon atoms.

Particularly preferably, the agent (a) comprises at least one organic silicon compound (a1) selected from silanes having one, two or three silicon atoms, the organic silicon compound comprising one or more hydroxyl groups and/or hydrolysable groups per molecule.

These organic silicon compounds (a1) or organic silanes included in the agent (a) is reactive compounds.

Organic silicon compounds, alternatively called organo-silicone compounds, are compounds which either have a direct silicon-carbon bond (Si—C) or in which the carbon is bonded to the silicon atom via an oxygen, nitrogen, or sulfur atom. The organic silicon compounds of the present disclosure are compounds comprising one to three silicon atoms. Organic silicon compounds preferably contain one or two silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

In a particularly preferred embodiment, an agent (a) is applied to the keratinous material, said agent (a) comprising at least one organic silicon compound (a1) selected from silanes having one, two or three silicon atoms, said organic silicon compound further comprising one or more hydroxyl groups or hydrolysable groups per molecule.

In a very particularly preferred embodiment, an agent (a) is applied to the keratinous material, said agent (a) comprising at least one organic silicon compound (a1) selected from silanes having one, two or three silicon atoms, said organic silicon compound further comprising one or more basic chemical functions and one or more hydroxyl groups or hydrolysable groups per molecule.

This basic group or basic chemical function can be, for example, an amino group, an alkylamino group, a dialkylamino group or a trialkyl amino group, which is preferably connected to a silicon atom via a linker. Preferably, the basic group is an amino group, a $C_1$-$C_6$ alkylamino group or a Di($C_1$-$C_6$)alkylamino group.

The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably comprises a structural unit R'R"R'"Si—O—$CH_2$—$CH_3$. The radicals R', R" and R'" represent the three remaining free valences of the silicon atom.

in a very particularly preferred method, the agent (a) comprises at least one organic silicon compound selected from silanes having one, two or three silicon atoms, the organic silicon compound preferably comprising one or more basic chemical functions and one or more hydroxyl groups or hydrolysable groups per molecule.

Particularly satisfactory results were obtained when the agent (a) comprises at least one organic silicon (a1) compound of formula (I) and/or (II).

The compounds of formulas (I) and (II) are organic silicon compounds selected from silanes having one, two or three silicon atoms, the organic silicon compound comprising one or more hydroxyl groups and/or hydrolysable groups per molecule.

In another very particularly preferred embodiment, the agent (a) comprises at least one organic silicon compound (a) of formula (I) and/or (II),

$$R_1R_2N\text{-}L\text{-}Si(OR_3)_a(R_4)_b \qquad (I),$$

where $R_1$, $R_2$ independently represent a hydrogen atom or a $C_1$-$C_6$ alkyl group, L is a linear or branched bivalent $C_1$-$C_{20}$ alkylene group, $R_3$ is a hydrogen atom or a $C_1$-$C_6$ alkyl group, $R_4$ represents a $C_1$-$C_6$ alkyl group a, represents an integer from 1 to 3, and b stands for the integer 3-a,

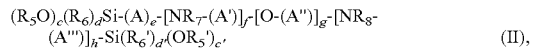

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \qquad (II),$$

where $R_5$, $R_5'$, $R_5''$ independently represent a hydrogen atom or for a $C_1$-$C_6$ alkyl group, $R_6$, $R_6'$ and $R_6''$ independently of one another represent a $C_1$-$C_6$ alkyl group, A, A', A", A''' and A'''' independently represent a linear or divalent, bivalent $C_1$-$C_{20}$ alkylene group, $R_7$ and $R_5$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

$$(A'''')\text{—}Si(R_6'')_{d''}(OR_5'')_{c''} \qquad (III),$$

c, stands for an integer from 1 to 3, d stands for the integer 3-c, c' stands for an integer from 1 to 3, d' stands for the integer 3-c', c" stands for an integer from 1 to 3, d" stands for the integer 3-c", e stands for 0 or 1, f stands for 0 or 1, g stands for 0 or 1, h stands for 0 or 1, provided that at least one of the radicals e, f, g, and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A''' and A'''' in the compounds of formula (I) and (II) are explained below as examples: Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—CH($CH_3$)—) and (—$CH_2$—CH($CH_3$)—$CH_2$—).

In the organic silicon compounds of the formula (I)

$$R_1R_2N\text{-}L\text{-}Si(OR_3)_a(R_4)_b \qquad (I),$$

the radicals $R_1$ and $R_2$ independently of one another represent a hydrogen atom or a $C_1$-$C_6$ alkyl group. Most preferably, the radicals $R_1$ and $R_2$ both represent a hydrogen atom.

In the middle part of the organic silicon compound is the structural unit or the linker -L- which stands for a linear or branched, divalent $C_1$-$C_{20}$ alkylene group.

A divalent $C_1$-$C_{20}$ alkylene group may alternatively be referred to as a divalent or divalent $C_1$-$C_{20}$ alkylene group, by which is meant that each L grouping may form two bonds. One bond is from the amino group $R_1R_2N$ to the linker L, and the second bond is between the linker L and the silicon atom.

Preferably, -L- represents a linear, divalent (i.e., divalent) $C_1$-$C_{20}$ alkylene group. Further preferably -L- stands for a linear bivalent $C_1$-$C_6$ alkylene group. Particularly preferred -L- stands for a methylene group ($CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The linear propylene group (—$CH_2$—$CH_2$—$CH_2$—) can alternatively be referred to as the propane-1,3-diyl group.

The organic silicon compounds of formula (I)

$$R_1R_2N\text{-}L\text{-}Si(OR_3)_a(R_4)_b \qquad (I),$$

one end of each carries the silicon-comprising group —Si$(OR_3)_a(R_4)_b$.

In the terminal structural unit $-\text{Si}(\text{OR}_3)_a(\text{R}_4)_b$, $R_3$ is hydrogen or $C_1$-$C_6$ alkyl group, and $R_4$ is $C_1$-$C_6$ alkyl group. $R_3$ and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Particularly resistant films could be produced if the agent (a) comprises at least one organic silicon compound (a1) of formula (I) in which the radicals $R_3$, $R_4$ independently of one another represent a methyl group or an ethyl group.

When using the process for dyeing keratinous material, dyeing with the best wash fastnesses could be obtained analogously when the agent (a) comprises at least one organic silicon compound of formula (I) in which the radicals $R_3$, $R_4$ independently of one another represent a methyl group or an ethyl group.

Furthermore, dyeing with the best wash fastnesses could be obtained if the agent (a) comprises at least one organic silicon compound of the formula (I) in which the radical a represents the number 3. In this case the radial b stands for the number 0.

In a further preferred embodiment, the agent (a) used in the process comprises at least one organic silicon compound (a1) of formula (I), wherein
- $R_3$, $R_4$ independently of one another represent a methyl group or an ethyl group and
- a stands for the number 3 and
- b stands for the number 0.

In another preferred embodiment, the agent (a) comprises at least one organic silicon compound (a1) of formula (I),

where
- $R_1$, $R_2$ both represent a hydrogen atom, and
- L represents a linear, bivalent $C_1$-$C_6$-alkylene group, preferably a propylene group ($-CH_2-CH_2-CH_2-$) or an ethylene group ($-CH_2-CH_2-$),
- $R_3$ represents a hydrogen atom, an ethyl group, or a methyl group,
- $R_4$ represents a methyl group or an ethyl group,
- a stands for the number 3 and
- b stands for the number 0.

Organic silicon compounds of the formula (I) which are particularly suitable for solving the problem as contemplated herein are

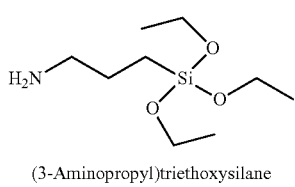

(3-Aminopropyl)triethoxysilane

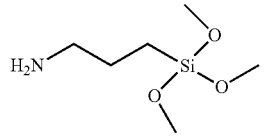

(3-Aminopropyl)trimethoxysilane

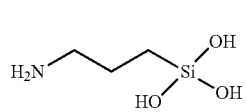

1-(3-Aminopropyl)silantriol

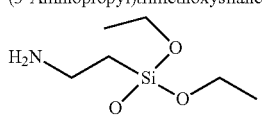

(2-Aminoethyl)triethoxysilane

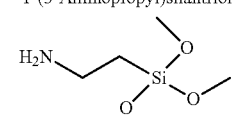

(2-Aminoethyl)trimethoxysilane

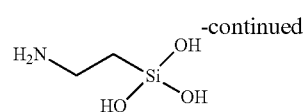

1-(2-Aminoethyl)silantriol

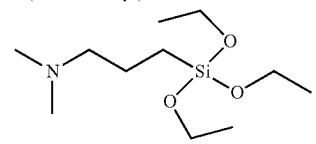

(3-Dimethylaminopropyl)triethoxysilane

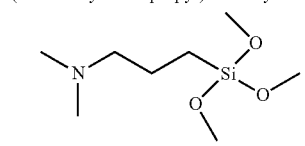

(3-Dimethylaminopropyl)trimethoxysilane

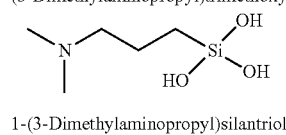

1-(3-Dimethylaminopropyl)silantriol

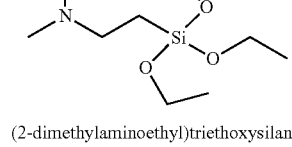

(2-dimethylaminoethyl)triethoxysilane.

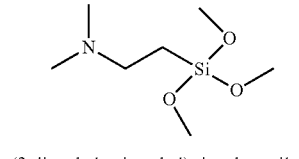

(2-dimethylaminoethyl)trimethoxysilane and

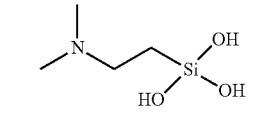

1-(2-Dimethylaminoethyl)silantriol

In a further preferred embodiment, the agent (a) comprises at least one organic silicon compound (a1) selected from the group of
- (3-Aminopropyl)triethoxysilane,
- (3-Aminopropyl)trimethoxysilane,
- 1-(3-Aminopropyl)silantriol,
- (2-Aminoethyl)triethoxysilane,
- (2-Aminoethyl)trimethoxysilane,
- 1-(2-Aminoethyl)silantriol,
- (3-Dimethylaminopropyl)triethoxysilane,
- (3-Dimethylaminopropyl)trimethoxysilane,
- 1-(3-Dimethylaminopropyl)silantriol,
- (2-Dimethylaminoethyl)triethoxysilane,
- (2-Dimethylaminoethyl)trimethoxysilane, and/or
- 1-(2-dimethylaminoethyl)silanetriol.

The organic silicon compounds of formula (I) are commercially available. (3-aminopropyl)trimethoxysilane, for example, can be purchased from Sigma-Aldrich. Also (3-aminopropyl)triethoxysilane is commercially available from Sigma-Aldrich.

In a further embodiment, the agent comprises at least one organic silicon compound (a1) of formula (II)

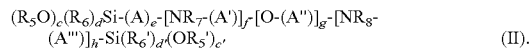

The organosilicon compounds of formula (II) each bear at their two ends the silicon-comprising groupings $(R_5O)_c(R_6)_d Si—$ and $—Si(R_6')_{d'}(OR_5')_{c'}$.

In the central part of the molecule of formula (II) there are the groups $-(A)_e-$ and $—[NR_7-(A')]_f-$ and $—[O-(A'')]_g—$ and $—[NR_8-(A''')]_h—$. Here, each of the radicals e, f, g, and h can independently of one another stand for the number 0 or 1, with the proviso that at least one of the radicals e, f, g, and h is different from 0. In other words, an organic silicon compound of formula (II) comprises at least one grouping selected from the group of $-(A)-$ and $—[NR_7-(A')]-$ and $—[O-(A'')]—$ and $—[NR_8-(A''')]—$.

In the two terminal structural units $(R_5O)_c(R_6)_d Sii-$ and $—Si(R_6')_{d'}(OR_5')_{c'}$, the radicals R5, R5', R5" independently of one another represent a hydrogen atom or a $C_1$-$C_6$ alkyl group. The radicals R6, R6' and R6" independently represent a $C_1$-$C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Films with the highest stability or dyes with the best wash fastnesses could be obtained when the radicals c and c' both stand for the number 3. In this case d and d' both stand for the number 0.

In another preferred embodiment, the agent (a) comprises at least one organic silicon compound (a1) of formula (II),

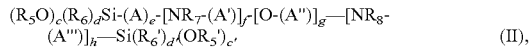

where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

$(R_5O)_3Si-(A)_e-[NR_7-(A')]_f-[O-(A'')]_g-[NR_8-(A''')]_h—Si(OR_5')_3$ (IIa).

The radicals e, f, g, and h can independently stand for the number 0 or 1, whereby at least one radical from e, f, g, and h is different from zero. The abbreviations e, f, g, and h thus define which of the groupings $-(A)_e-$ and $—[NR_7-(A')]_f-$ and $—[O-(A'')]_g-$ and $—[NR_8-(A''')]_h-$ are in the middle part of the organic silicon compound of formula (II).

In this context, the presence of certain groupings has proved to be particularly beneficial in terms of increasing washability. Particularly satisfactory results were obtained when at least two of the radicals e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

$(R_5O)_c(R_6)_d Si-(A)-[NR_7-(A')]—Si(R_6')_{d'}(OR_5')_{c'}$ (IIb).

The radicals A, A', A", A''' and A'''' independently represent a linear or divalent, bivalent $C_1$-$C_{20}$ alkylene group. Preferably the radicals A, A', A", A''' and A'''' independently of one another represent a linear, bivalent $C_1$-$C_{20}$ alkylene group. Further preferably the radicals A, A', A", A''' and A'''' independently represent a linear bivalent $C_1$-$C_6$ alkylene group. In particular, the radicals A, A', A", A''' and A'''' independently of one another represent a methylene group ($—CH_2—$), an ethylene group ($—CH_2—CH_2—$), a propylene group ($—CH_2—CH_2—CH_2—$) or a butylene group ($—CH_2—CH_2—CH_2—CH_2—$). Very preferably, the radicals A, A', A", A''' and A'''' represent a propylene group ($—CH_2—CH_2—CH_2—$).

The divalent $C_1$-$C_{20}$ alkylene group may alternatively be referred to as a divalent or divalent $C_1$-$C_{20}$ alkylene group, by which is meant that each grouping A, A', A", A''' and A'''' may form two bonds.

The linear propylene group ($—CH_2—CH_2—CH_2—$) can alternatively be referred to as the propane-1,3-diyl group.

If the radical f represents the number 1, then the organic silicon compound of formula (II) comprises a structural grouping $—[NR_7-(A')]-$.

If the radical h represents the number 1, then the organic silicon compound of formula (II) comprises a structural grouping $—[NR_8-(A''')]-$.

Wherein radicals $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (III)

$(A''')—Si(R_6'')_{d''}(OR_5'')_{c''}$ (III).

Very preferably the radicals $R_7$ and $R_8$ independently of one another represent a hydrogen atom, a methyl group, a 2-hydroxyethyl group, a 2-alkenyl group, a 2-aminoethyl group or a grouping of the formula (III).

If the radical f represents the number 1 and the radical h represents the number 0, the organic silicon compound comprises the grouping $[NR_7-(A')]$ but not the grouping $—[NR_8-(A''')]$. If the radical R7 now stands for a grouping of the formula (III), the agent (a) comprises an organic silicon compound with 3 reactive silane groups.

In another preferred embodiment, the agent (a) comprises at least one organic silicon compound (a1) of formula (II),

where
e and f both stand for the number 1,
g and h both stand for the number 0,
A and A' independently represent a linear, divalent $C_1$-$C_6$ alkylene group and
$R_7$ represents a hydrogen atom, a methyl group, a 2-hydroxyethyl group, a 2-alkenyl group, a 2-aminoethyl group or a group of formula (III).

In a further preferred embodiment, the agent (a) comprises at least one organic silicon compound of formula (II), wherein
e and f both stand for the number 1,
g and h both stand for the number 0,
A and A' independently of one another represent a methylene group ($—CH_2—$), an ethylene group ($—CH_2—CH_2—$) or a propylene group ($—CH_2—CH_2—CH_2$), and
$R_7$ represents a hydrogen atom, a methyl group, a 2-hydroxyethyl group, a 2-alkenyl group, a 2-aminoethyl group or a group of formula (III).

Organic silicon compounds of formula (II) which are well suited for solving the problem as contemplated herein are:

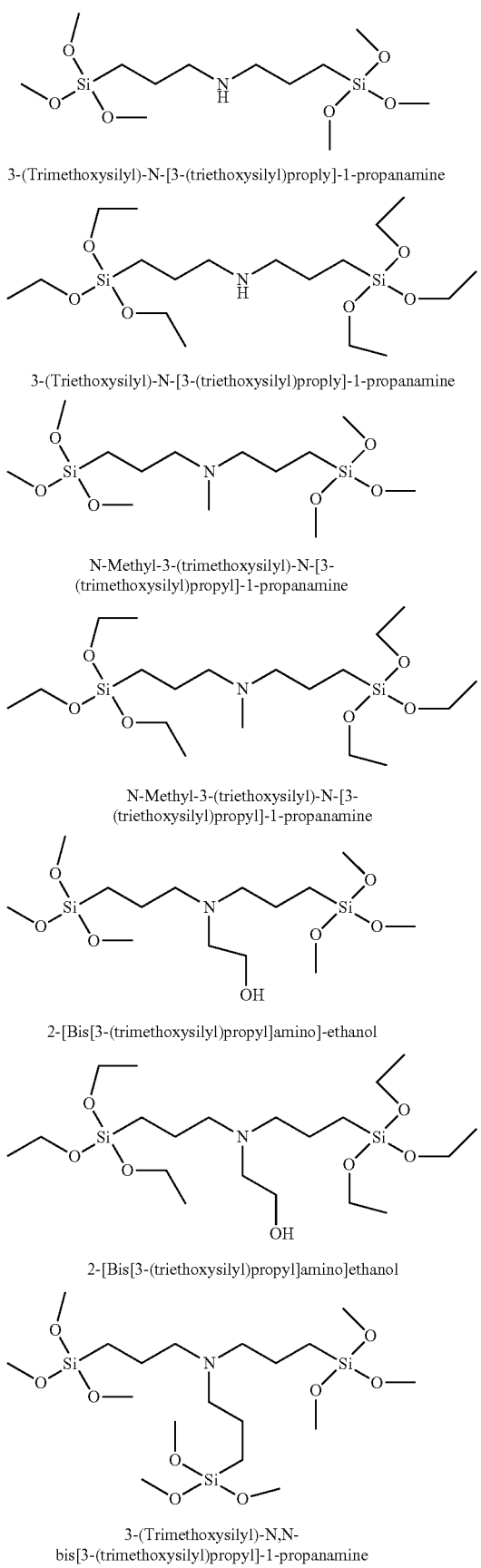
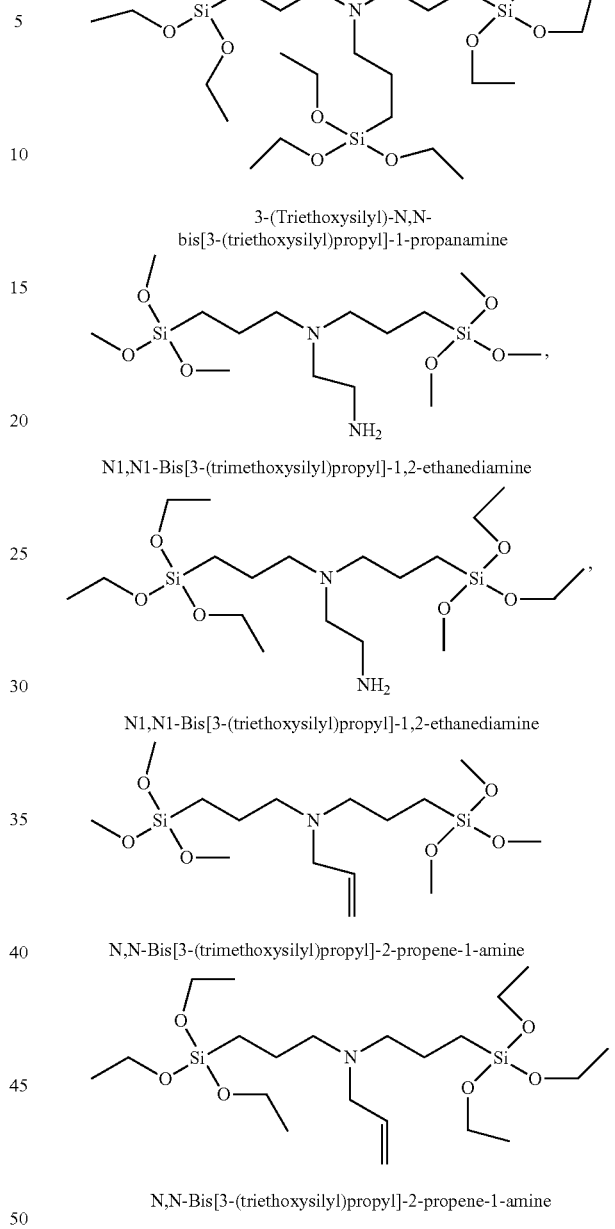

The organic silicon compounds of formula (II) are commercially available.

Bis(trimethoxysilylpropyl)amines with the CAS number 82985-35-1 can be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased for example from Fluorochem or Sigma-Aldrich.

In a further preferred embodiment, the agent (a) comprises at least one organic silicon compound (a1) selected from the group of 3-(Trimethoxysilyl)-N-[3-(trimethoxysilyl)propyl]-1-propanamine,
3-(Triethoxysilyl)-N-[3-(triethoxysilyl)propyl]-1-propanamine,
N-Methyl-3-(trimethoxysilyl)-N-[3-(trimethoxysilyl)propyl]-1-propanamine,
N-Methyl-3-(triethoxysilyl)-N-[3-(triethoxysilyl) propyl]-1-propanamine,
2-[Bis[3-(trimethoxysilyl)propyl]amino]-ethanol,
2-[Bis[3-(triethoxysilyl)propyl]amino]ethanol,
3-(Trimethoxysilyl)-N,N-bis[3-(trimethoxysilyl)propyl]-1-propanamine,
3-(Triethoxysilyl)-N,N-bis[3-(triethoxysilyl)propyl]-1-propanamine,
N1,N1-Bis[3-(trimethoxysilyl)propyl]-1,2-ethanediamine,
N1,N1-Bis[3-(triethoxysilyl)propyl]-1,2-ethanediamine,
N,N-Bis[3-(trimethoxysilyl)propyl]-2-Propen-1-amine, and/or
N,N-Bis[3-(triethoxysilyl)propyl]-2-propen-1-amine.

In further tests, in particular dyeing tests, it has also been found to be particularly advantageous if the agent (a) applied to the keratinous material in the process comprises at least one organic silicon compound of the formula (IV)

         (IV).

The compounds of formula (IV) are organic silicon compounds selected from silanes having one, two or three silicon atoms, the organic silicon compound comprising one or more hydroxyl groups and/or hydrolysable groups per molecule.

The organic silicon compound(s) of formula (IV) may also be called a silane of the alkyl-alkoxy-silane or alkyl-hydroxy-silane type,

         (IV), where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

In a further preferred embodiment, the agent (a) comprises at least one organic silicon compound (a1) of formula (IV)

         (IV), where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

In a further preferred embodiment, the agent (a) comprises, in addition to the organic silicon compound or compounds of formula (I), at least one further organic silicon compound of formula (IV)

         (IV), where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

In a further preferred embodiment, the agent (a) comprises, in addition to the organic silicon compound or compounds of formula (II), at least one further organic silicon compound of formula (IV)

         (IV), where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

In a further preferred embodiment, the agent (a) comprises, in addition to the organic silicon compound or compounds of formula (I) and/or (II), at least one further organic silicon compound of formula (IV)

         (IV), where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

In the organic silicon compounds of formula (IV), the radical R$_9$ represents a C$_1$-C$_{18}$ alkyl group. This C$_1$-C$_{18}$ alkyl group is saturated and can be linear or branched. Preferably, R$_9$ represents a linear C$_1$-C$_{18}$ alkyl group. Preferably, R$_9$ represents a methyl group, an ethyl group, an n-propyl group, an n-butyl group, an n-pentyl group, an n-hexyl group, an n-octyl group, an n-dodecyl group or an n-octadecyl group. Particularly preferably, R$_9$ represents a methyl group, an ethyl group, an n-hexyl group or an n-octyl group.

In the organic silicon compounds of form (IV), the R$_{10}$ radical represents a hydrogen atom or a C$_1$-C$_6$ alkyl group. Especially preferably, R$_{10}$ stands for a methyl group or an ethyl group.

In the organic silicon compounds of form (IV), the radical R$_{11}$ represents a C$_1$-C$_6$ alkyl group. Particularly preferably, R$_{11}$ represents a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Particularly stable films, i.e., dyeing with particularly good wash fastness properties, could be obtained if an agent (a) comprising at least one organic silicon compound (a1) corresponding to formula (IV): in which the radical k is the number 3, was used in the process. In this case the radical m stands for the number 0.

Organic silicon compounds of the formula (IV) which are particularly suitable for solving the problem as contemplated herein are

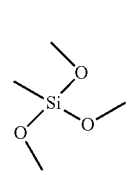 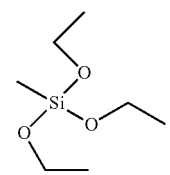

Methyltrimethoxysilane    Methyltriethoxysilane

-continued

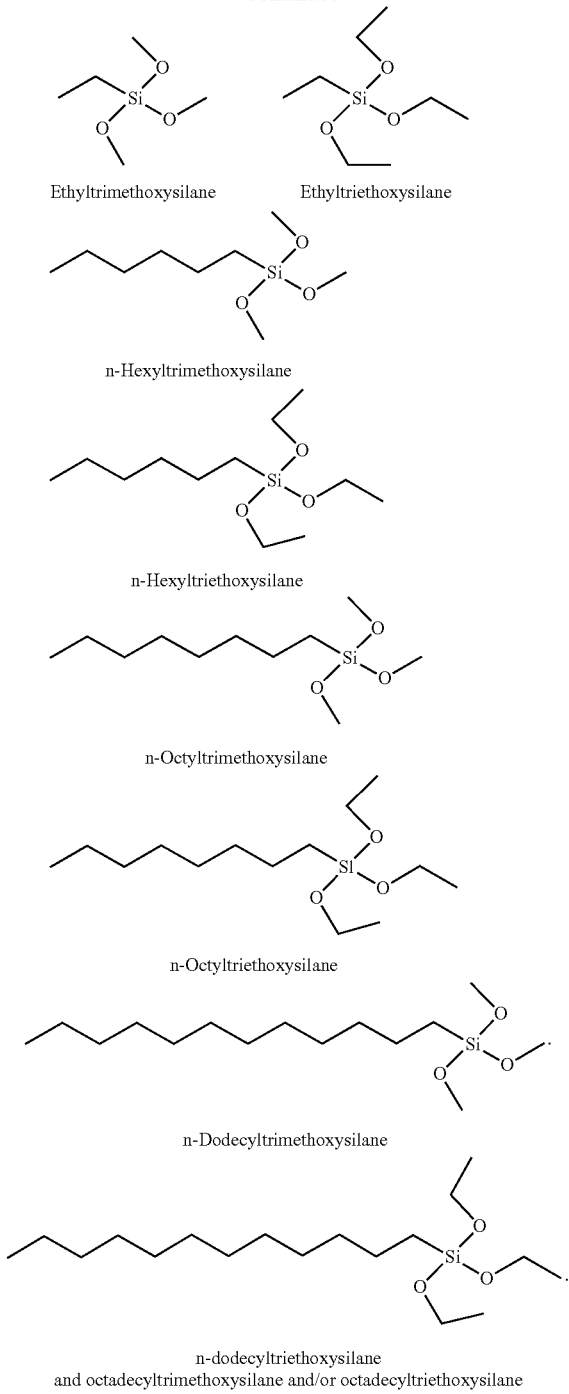

Ethyltrimethoxysilane
Ethyltriethoxysilane
n-Hexyltrimethoxysilane
n-Hexyltriethoxysilane
n-Octyltrimethoxysilane
n-Octyltriethoxysilane
n-Dodecyltrimethoxysilane
n-dodecyltriethoxysilane
and octadecyltrimethoxysilane and/or octadecyltriethoxysilane In another preferred embodiment, the agent (a) comprises at least one organic silicon compound (a1) of formula (IV) selected from the group of
Methyltrimethoxysilane,
Methyltriethoxysilane,
Ethyltrimethoxysilane,
Ethyltriethoxysilane,
Propyltrimethoxysilane,
Propyltriethoxysilane,
Hexyltrimethoxysilane,
Hexyltriethoxysilane,
Octyltrimethoxysilane,
Octyltriethoxysilane,
Dodecyltrimethoxysilane,
Dodecyltriethoxysilane,
Octadecyltrimethoxysilane, and/or
Octadecyltriethoxysilane.

The organic silicon compounds described above are reactive compounds. In this context, it has been found preferable if the agent (a) comprises—based on the total weight of the agent (a)—one or more organic silicon compounds (a1) in a total amount of 0.1 to 20 wt. %, preferably 1 to 15 wt. % and particularly preferably 2 to 8 wt. %.

In a further preferred embodiment, the agent (a) comprises—based on the total weight of the agent (a)—one or more organic silicon compounds (a1) in a total amount of 0.1 to 20 wt. %, preferably 1 to 15 wt. % and particularly preferably 2 to 8 wt. %.

To achieve particularly good dyeing results, it is particularly advantageous to use the organic silicon compounds of the formula (I) and/or (II) in certain quantity ranges on agent (a). Particularly preferably, the agent (a) comprises—based on the total weight of the agent (a)—one or more organic silicon compounds of the formula (I) and/or (II) in a total amount of 0.1 to 10 wt. %, preferably 0.5 to 5 wt. % and particularly preferably 0.5 to 3 wt. %.

In a further preferred embodiment, the agent (a) comprises—based on the total weight of the agent (a)—one or more organic silicon compounds of the formula (I) and/or (II) in a total amount of 0.1 to 10 wt. %, preferably 0.5 to 5 wt. % and particularly preferably 0.5 to 3 wt. %.

Furthermore, it has proven to be particularly preferred if the organic silicon compound(s) of formula (IV) is (are) also present in certain quantity ranges in agent (a). Particularly preferably, the agent (a) comprises—based on the total weight of the agent (a)—one or more organic silicon compounds of the formula (IV) in a total amount of 0.1 to 20 wt. %, preferably 2 to 15 wt. % and particularly preferably 4 to 9 wt. %.

In a further preferred embodiment, the agent (a) comprises—based on the total weight of the agent (a)—one or more organic silicon compounds of the formula (IV) in a total amount of 0.1 to 20 wt. %, preferably 2 to 15 wt. % and particularly preferably 3.2 to 10 wt. %.

In the course of the work leading to this present disclosure, it was found that particularly stable and uniform films could be obtained on the keratinous material even when the agent (a) included two organic silicon compounds that were structurally different from each other.

In another preferred embodiment, the agent (a) comprises at least two structurally different organic silicon compounds.

In a preferred embodiment, an agent (a) comprising at least one organic silicon compound of formula (I) and at least one organic silicon compound of formula (IV) is applied to the keratinous material.

In an explicitly very particularly preferred embodiment, the agent (a) comprises at least one organic silicon compound of formula (I) selected from the group of (3-aminopropyl)triethoxysilane and (3-aminopropyl)trimethoxysilane and additionally comprising at least one organic silicon compound of formula (IV) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane and hexyltriethoxysilane.

In a further preferred embodiment, the agent (a) comprises—based on the total weight of the agent (a):
0.5 to 5 wt. % % of at least one first organic silicon compound (a1) which is selected from the group of (3-aminopropyl)trimethoxysilane, (3-aminopropyl)triethoxysilane, (2-aminoethyl)trimethoxysilane, (2-aminoethyl)triethoxy silane, (3-dimethylaminopropyl) trimethoxysilane, (3-dimethylaminopropyl) triethoxysane (2-dimethylaminoethyl)trimethoxysilane and (2-dimethylaminoethyl)triethoxysilane, and 3.2 to 10 wt. % of at least one second organic silicon compound (a1) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In this embodiment, the agent (a) comprises one or more organic silicon compounds of a first group in a total amount of 0.5 to 5 wt. %. The organic silicon compounds of this first group are selected from the group of (3-aminopropyl) trimethoxysilane, (3-aminopropyl)triethoxysilane, (2-aminoethyl)trimethoxysilane, (2-aminoethyl)triethoxysilane, (3-dimethyl aminopropyl)trimethoxysilane, (3-dimethylaminopropyl)triethoxysilane (2-dimethylaminoethyl) trimethoxysilane and/or (2-di methyl amino ethyl)triethoxysilane.

In this embodiment, the agent (a) comprises one or more organic silicon compounds of a second group in a total amount of 3.2 to 10 wt. %. The organic silicon compounds of this second group are selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, do decyltrimethoxysilane, dodecyltriethoxysilane, octadecyltrimethoxysilane and octadecyltriethoxysilane.

Even the addition of insignificant amounts of water leads to hydrolysis in organic silicon compounds with at least one hydrolysable group. The hydrolysis products and/or organic silicon compounds having at least one hydroxy group may react with each other in a condensation reaction. For this reason, both the organosilicon compounds having at least one hydrolysable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolysable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly satisfactory results were obtained when organic silicon compounds of formula (I) and/or (II) were used in the process. Since, as already described above, hydrolysis/condensation already starts at traces of moisture, the hydrolysis and/or condensation products of the organic silicon compounds (I) and/or (II) are also included in this embodiment.

Phosphoric Acid Ester (a2)

When the agent (a) is applied to the keratinous material, the organic silicon compound(s) (a1), which preferably comprise one or more hydroxyl groups or hydrolysable groups per molecule, are first hydrolyzed and oligomerized or polymerized in the presence of water. The hydrolysis products or oligomers formed in this way have a particularly high affinity for the surface of the keratinous material. If phosphoric acid esters (a2) are simultaneously present in the agent (a), it is presumed that they will be integrated into the resulting oligomers or polymers. If the agent (a) further comprises at least one colorant compound, the film formed on the keratinous material is a colored film. Following the application of agent (a), agent (b) is now applied, whereby the sealing reagent included in this agent (b) seals the, colored, film. If the agent (b) further comprises at least one colorant compound, either the uncolored film produced in the first step is sealed and colored, or the color impression of the colored film produced in the first step is enhanced or modified, depending on the colorant compound used, or the color impression of the first film is enhanced or modified by forming a second, colored film on the first, colored film. If the agent (b) does not contain a colorant compound, the colored film prepared in the first step is sealed. Successive application of agents (a) and (b) produces a coloration that is particularly resistant to external influences.

As an essential component (a2) of the present disclosure, the agent (a) used in the dyeing process comprises at least one phosphoric acid ester.

It has been shown that phosphoric acid esters improve the exhaustion behavior of the coloring compound and thus particularly uniform and stable colorations can be obtained.

Phosphoric acid esters are esters of orthophosphoric acid, which are formally or formed by the reaction of the acid and alcohols with elimination of water. A distinction is made between monoesters, diesters and triesters. Monoesters are formed by the reaction of the alcohol with polyphosphoric acid, while mixtures of monoesters and diesters are prepared by reacting the alcohol with phosphorus pentoxide.

The esters of orthophosphoric acid with aliphatic alcohols can be used as phosphoric acid esters. The aliphatic alcohols are linear or branched, saturated or unsaturated alcohols with 1 to 22 carbon atoms and 0, 1, 2 or 3 double bonds. Typical representatives are, for example, methanol, ethanol, n-propanol, isopropanol, n-butanol, sec.-butanol, tert. butanol, n-pentanol, capric alcohol, caprylic alcohol, 2-ethylhexanol, capric alcohol, myristyl alcohol, lauryl alcohol, cetyl alcohol, palmitoleyl alcohol, stearyl alcohol, oleyl alcohol, elaidyl alcohol, petroselyl alcohol, linolyl alcohol, linolenyl alcohol, behenyl alcohol or erucyl alcohol. Preferably, the aliphatic alcohols are branched and saturated alcohols with 11 to 14 carbon atoms. Very preferably, the aliphatic alcohols are a mixture of branched and saturated alcohols with 11 to 14 carbon atoms, which has a high proportion of isotridecanol.

Accordingly, in a preferred embodiment, the agent (a) comprises at least one phosphoric acid ester (a2) selected from the group of esters of orthophosphoric acid with aliphatic alcohols.

In a particularly preferred embodiment, the agent (a) comprises at least one phosphoric acid ester (a2) comprising an ester of orthophosphoric acid with a branched aliphatic alcohol having 11 to 14 carbon atoms.

A particularly suitable phosphoric acid ester (a2) that can be used in the process is phosfetal 218 (CAS no: 154518-38-4, Phosphoric acid, C11-14-isoalkyl esters, C13-rich), which is available from Zschimmer & Schwarz.

Alternatively, the esters of orthophosphoric acid with alkoxylated aliphatic alcohols or the esters of orthophosphoric acid with alkoxylated phenols can be used as phosphoric acid esters. The alkoxylated alcohols are ethoxylated alcohols with 1 to 22 carbon atoms.

Accordingly, in an equally preferred embodiment, the agent (a) comprises at least one phosphoric acid ester (a2) selected from the group of esters of orthophosphoric acid with ethoxylated having 1 to 22 carbon atoms.

In a particularly preferred embodiment, the agent (a) comprises at least one phosphoric acid ester (a2) comprising an ester of orthophosphoric acid with an ethoxylated aliphatic alcohol having 8 to 18 carbon atoms.

The average degree of ethoxylation of the aliphatic alcohols is preferably in the range from 2 to 80 and more preferably in the range from 5 to 25.

A particularly suitable phosphoric acid ester (a2) that can be used in the process is Crodafos SP (INCI: Ceteth-20 Phosphate), which is available from Croda.

The alkoxylated phenols are preferably ethoxylated phenols or ethoxylated alkylphenols.

Particularly satisfactory results could be obtained if the agent (a)—based on the total weight of the agent (a)—comprises one or more phosphoric acid esters (a2) in a total amount of from 0.1 to 30 wt. %, preferably from 0.5 to 25 wt. % and very preferably from 0.75 to 20 wt. %.

The total amount of phosphoric acid ester (a2) in agent (a) may also depend on the type of phosphoric acid ester used.

When using a phosphoric acid ester (a2) selected from the group of esters of orthophosphoric acid with an aliphatic alcohol, in particular when using an ester of orthophosphoric acid with a branched, aliphatic alcohol having 11 to 14 carbon atoms, particularly good results could be obtained if the Means (a)—based on the total weight of the pigment suspension—comprises the phosphoric acid ester (a2) in a total amount of 1 to 30 wt. %, preferably 5 to 25 wt. % and very particularly preferably 10 to 20 wt. %.

In another particularly preferred embodiment, the agent (a) comprises—based on the total weight of the agent (a)—one or more phosphoric acid esters (a2) selected from the group of esters of orthophosphoric acid with a branched, aliphatic alcohol having 11 to 14 carbon atoms in a total amount of from 1 to 30 wt. %, preferably from 5 to 25 wt. % and most preferably from 10 to 20 wt. %.

When using a phosphoric acid ester (a2) selected from the group of esters of orthophosphoric acid with an ethoxylated, aliphatic alcohol having 1 to 22 carbon atoms, especially when using a phosphoric acid ester (a2) with the INCI designation Ceteth-20 phosphate, particularly good results could be achieved could be obtained if the agent (a)—based on the total weight of the pigment suspension—contaons the phosphoric acid ester (a2) in a total amount of 0.1 to 10 wt. %, preferably 0.5 to 7.5 wt. %, more preferably from 0.75 to 5 wt. % and most preferably from 1 to 2.5 wt. %.

In a further particularly preferred embodiment, the agent (a)—based on the total weight of the pigment suspension—one or more phosphoric acid esters (a2) selected from the group of esters of orthophosphoric acid with an ethoxylated, aliphatic alcohol with 1 to 22 carbon atoms, contains preferably a phosphoric acid ester (a2) with the INCI designation Ceteth-20 phosphate, in a total amount of 0.1 to 10 wt. %, preferably 0.5 to 7.5 wt. %, more preferably of 0.75 to 5 wt. % and most preferably from 1 to 2.5 wt. %.

Agent (b)

The method of treatment of keratinous material includes, in addition to the application of agent (a), the application of agent (b). The agent (b) comprises at least one sealing reagent (b1).

The agent (b) is a post-treatment agent and the application of agent (b) to the keratinous material treated with agent (a) has the effect of making the colorations obtained in the process more durable. In particular, the use of agent (b) can improve the fastness to washing and the fastness to rubbing of the dyeing obtained in the process.

It is preferred that the sealing reagent comprises a compound selected from the group of film forming polymers, alkalizing agents, acidifying agents, and mixtures thereof.

It may be preferred that the sealing reagent comprises a film-forming polymer.

Polymers are macromolecules with a molecular weight of at least 1000 g/mol, preferably of at least 2500 g/mol, particularly preferably of at least 5000 g/mol, which include identical, repeating organic units. The polymers of the present disclosure may be synthetically produced polymers which are manufactured by polymerization of one type of monomer or by polymerization of several types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. In terms of the present disclosure, it is preferred if the maximum molecular weight of the film-forming polymer as sealing reagent (b1) is not more than 107 g/mol, preferably not more than 106 g/mol, and particularly preferably not more than 105 g/mol.

As contemplated herein, a film-forming polymer is a polymer which can form a film on a substrate, for example on a keratinic material or a keratinic fiber. The formation of a film can be demonstrated, for example, by viewing the polymer-treated keratinous material under a microscope.

The film-forming polymers (b1) in the agent (b) can be hydrophilic or hydrophobic.

In a first embodiment, it may be preferred to use at least one hydrophobic film-forming polymer in agent (b).

A hydrophobic polymer is a polymer that has a solubility in water at 25° C. (760 mmHg) of less than 1 wt. %.

The water solubility of the film-forming, hydrophobic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1 wt. %.

These include acrylic acid-type polymers, polyurethanes, polyesters, polyamides, polyureas, cellulose polymers, nitrocellulose polymers, silicone polymers, acrylamide-type polymers, and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a composition (b) comprises at least one film-forming, hydrophobic polymer (b1) selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters, or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, ethyl (meth)acrylate, methyl (meth)acrylate, tert-butyl (meth)acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, those with $C_2$-$C_{18}$ alkyl groups, such as N-ethyl acrylamide, N-tert-butylacrylamide, le N-octylacrylamide, N-di(C1-C4)alkyl(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acryla-tes/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex OPT (Acrylates/C12-22 Alkyl methacrylate Copolymer).

Suitable polymers based on vinyl monomers may include, for example, the homopolymers and copolymers of N-vinylpyrrolidone, vinylcaprolactam, vinyl-($C_1$-$C_6$)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable olefin-based polymers include homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers comprising one or more blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Surprisingly, it was found that particularly intense and washfast colorations could be obtained when agent (b) included at least one film-forming polymer as sealing reagent (b1), which was selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, the agent (b) comprises at least one film-forming polymer as sealing agent (b1), which is selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer as sealing reagent (b1) in agent (b).

A hydrophilic polymer is a polymer that has a solubility in water at 25° C. (760 mmHg) of more than 1 wt. %, preferably more than 2 wt. %.

The water solubility of the film-forming, hydrophilic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1 wt. %.

Nonionic, anionic, and cationic polymers can be used as film-forming, hydrophilic polymers.

Suitable film-forming hydrophilic polymers may be selected, for example, from the group of polyvinylpyrrolidone (co)polymers, polyvinyl alcohol (co)polymers, vinyl acetate (co)polymers, the carboxyvinyl (co)polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-comprising copolymer as film-forming hydrophilic polymer.

In another very particularly preferred embodiment, an agent (b) comprises at least one film-forming hydrophilic polymer selected from the group of polyvinylpyrrolidone (PVP) and the copolymers of polyvinylpyrrolidone.

It is further preferred if the agent comprises polyvinylpyrrolidone (PVP) as the film-forming hydrophilic polymer. Surprisingly, the wash fastness of the stains obtained with PVP-comprising agents (b) was also particularly good.

Particularly well-suited polyvinylpyrrolidones are available, for example, under the name Luviskol® K from BASF SE, especially Luviskol® K 90 or Luviskol® K 85 from BASF SE.

The polymer PVP K30, which is marketed by Ashland (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF.

The use of film-forming hydrophilic polymers (b1) from the group of copolymers of polyvinylpyrrolidone has also led to particularly good and washfast color results.

Vinylpyrrolidone-vinyl ester copolymers, such as those marketed under the trademark Luviskol® (BASF), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-comprising copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-comprising copolymer.

Other suitable copolymers of polyvinylpyrrolidone may also be those obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In another very particularly preferred embodiment, an agent (b) comprises at least one film-forming hydrophilic polymer (b1) selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another suitable copolymer of vinylpyrrolidone is the polymer known under the INCI designation maltodextrin/VP copolymer.

Furthermore, intensively colored keratinous material, especially hair, could be obtained with particularly good wash fastness properties when a nonionic film-forming hydrophilic polymer was used as the film-forming hydrophilic polymer.

In another embodiment, the agent (b) may comprise at least one nonionic film-forming hydrophilic polymer (b1).

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products comprising, as a nonionic, film-forming, hydrophilic polymer, at least one polymer selected from the group of Polyvinylpyrrolidone, Copolymers of N-vinylpyrrolidone and vinyl esters of carboxylic acids comprising 2 to 18 carbon atoms of N-vinylpyrrolidone and vinyl acetate, Copolymers of N-vinylpyrrolidone and N-vinylimidazole and methacrylamide, Copolymers of N-vinylpyrrolidone and N-vinylimidazole and acrylamide, Copolymers of N-vinylpyrrolidone with N,N-di(C1 to C4)alkylamino-(C2 to C4)alkyl acrylamide.

If copolymers of N-vinylpyrrolidone and vinyl acetate are used, it is again preferable if the molar ratio of the structural units included in the monomer N-vinylpyrrolidone to the structural units of the polymer included in the monomer vinyl acetate is in the range from 20:80 to 80:20, in particular from 30:70 to 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF SE.

Another particularly preferred polymer is selected from the INCI designation VP/Methacrylamide/Vinyl Imidazole Copolymer, which is available under the trade name Luviset Clear from BASF SE.

Another very particularly preferred nonionic, film-forming, hydrophilic polymer is a copolymer of N-vinylpyrrolidone and N,N-dimethylaminiopropylmethacrylamide, which is sold, for example, by the company ISP with the INCI designation VP/DMAPA Acrylates Copolymer, e.g., under the trade name Styleze® CC 10.

A cationic polymer is the copolymer of N-vinylpyrrolidone, N-vinylcaprolactam, N-(3-dimethyl aminopropyl) methacrylamide and 3-(methacryloylamino)propyllauryl dimethylammonium chloride (INCI designation: Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include
- Vinylpyrrolidone-vinylimidazolium methochloride copolymers, as offered under the designations Luviquat® FC 370, FC 550, and the INCI designation Polyquaternium-16 as well as FC 905 and HM 552,
- Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available for example under the name Luviquat® Hold from BASF SE. Polyquaternium-46 is preferably used in an amount of 1 to 5 wt. %—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol or under the names Synthalen M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the acrylamide group are, for example, polymers prepared from monomers of (meth)acrylamido-$C_1$-$C_4$-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of poly(meth)arylamido-$C_1$-$C_4$-alkylsulfonic acids are crosslinked and at least 90% neutralized. These polymers can be crosslinked or non-crosslinked.

Cross-linked and fully or partially neutralized polymers of the poly-2-acrylamido-2-methylpropane sulfonic acid type are known under the INCI designations "ammonium polyacrylamido-2-methylpropanesulphonates" or "ammonium polyacryldimethyltauramides".

Another preferred polymer of this type is the crosslinked poly-2-acrylamido-2methyl-propanesulfonic acid polymer sold by Clariant under the trade name Hostacerin AMPS, which is partially neutralized with ammonia.

In another explicitly very particularly preferred embodiment, the agent (b) comprises at least one anionic, film-forming, polymer (b1).

In this context, the best results were obtained when the agent (b) comprises, as sealing reagent (b1), at least one film-forming polymer comprising at least one structural unit of formula (P-I) and at least one structural unit of formula (P-II)

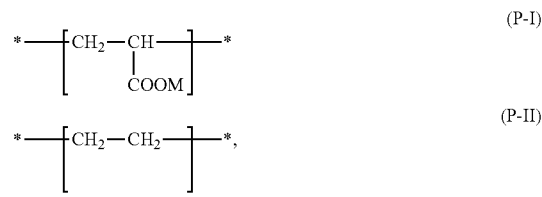

where
M is a hydrogen atom or ammonium ($NH_4$), sodium, potassium, ½ magnesium or ½ calcium.

In a further preferred embodiment, the agent (b) comprises at least one film-forming polymer as sealing reagent (b1), which comprises at least one structural unit of the formula (P-I) and at least one structural unit of the formula (P-II)

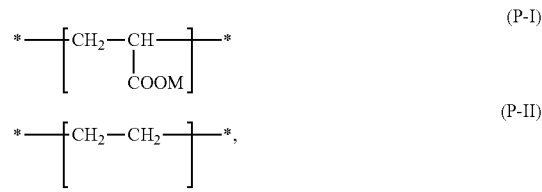

where
M is a hydrogen atom or ammonium ($NH_4$), sodium, potassium, ½ magnesium or ½ calcium.

When M represents a hydrogen atom, the structural unit of the formula (P-I) is based on an acrylic acid unit.

When M stands for an ammonium counterion, the structural unit of the formula (P-I) is based on the ammonium salt of acrylic acid.

When M stands for a sodium counterion, the structural unit of the formula (P-I) is based on the sodium salt of acrylic acid.

When M stands for a potassium counterion, the structural unit of the formula (P-I) is based on the potassium salt of acrylic acid.

If M stands for a half equivalent of a magnesium counterion, the structural unit of the formula (P-I) is based on the magnesium salt of acrylic acid.

If M stands for a half equivalent of a calcium counterion, the structural unit of the formula (P-I) is based on the calcium salt of acrylic acid.

The film-forming polymer or polymers (b1) are preferably used in certain ranges of amounts in the agent (b). In this context, it has proved particularly preferable for solving the problem as contemplated herein if the agent (b) comprises—based on the total weight of the agent (b)—one or more film-forming polymers (b1) in a total amount of from 0.1 to 18 wt. %, preferably from 1 to 16 wt. %, more preferably from 5 to 14.5 wt. % and very particularly preferably from 8 to 12 wt. %.

In a further preferred embodiment, the agent (b) comprises—based on the total weight of the agent (b)—one or more film-forming polymers (b1) in a total amount of from 0.1 to 18 wt. %, preferably from 1 to 16 wt. %, more preferably from 5 to 14.5 wt. % and very particularly preferably from 8 to 12 wt. %.

The application of agent (b) comprising a film-forming polymer as sealing reagent (b1) is intended to seal and/or fix the colored film initially produced by the application of agent (a). With application of the second agent (b) with a film-forming polymer as sealing reagent (b1), the film-forming polymer (b1) is deposited on the colored film produced in the first layer in the form of a further film. The multilayer film system created in this way exhibits improved resistance to external influences.

Here, the film produced by the agent (b) comprising a film-forming polymer as sealing reagent (b1) is preferably not colored itself. In this way, it can also be ensured that any abrasion to a certain extent of the second film formed by agent (b) does not lead to any color changes in the entire film system. It is therefore particularly preferred if the agent (b) comprises no or only lesser amounts of colorant compounds.

In an alternative embodiment, the sealing reagent (b1) comprises an alkalizing agent.

Particularly preferably, the alkalizing agent is selected from the group of ammonia, $C_2$-$C_6$ alkanolamines, basic amino acids, alkali metal hydroxides and alkaline earth metal hydroxides.

In another particularly preferred embodiment, the agent (b) comprises at least one alkalizing agent as sealing reagent (b1), which is selected from the group of ammonia, $C_2$-$C_6$ alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates and alkaline earth metal carbonates.

It has been found that aftertreatment with an agent (b) comprising ammonia exerts a particularly good influence on improving the wash fastness and rub fastness of the dyeing obtained in the process.

In the context of a further very particularly preferred embodiment, the agent (b) comprises ammonia as sealing reagent (b1).

Satisfactory results were also obtained when agent (b) included at least one $C_2$-$C_6$ alkanolamine as sealing reagent (b1).

The alkanolamines that can be used in agent (b) can be selected, for example, from the group of primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

In a further preferred embodiment, the agent (b) comprises, as sealing reagent (b1), at least one alkalizing agent from the group of alkanolamines, which is preferably selected from the group of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol and 2-amino-2-methylpropane-1,3-diol.

Likewise, satisfactory results were obtained when agent (b) included at least one basic amino acid as sealing reagent (b1).

For the purposes of the present disclosure, an amino acid is an organic compound comprising in its structure at least one protonatable amino group and at least one —COOH or one —$SO_3$H group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In a further particularly preferred embodiment, the sealing reagent (b1) is an alkalizing agent comprising a basic amino acid selected from the group of arginine, lysine, ornithine and/or histidine.

In a further preferred embodiment, the agent (b) comprises as sealing reagent (b1) at least one alkalizing agent selected from the group of basic amino acids, which is preferably selected from the group of arginine, lysine, ornithine, and histidine.

Satisfactory results were also obtained when the agent (b) included at least one alkali metal hydroxide as sealing reagent (b1). Examples of well-suited alkali metal hydroxides are sodium hydroxide and potassium hydroxide.

Satisfactory results were also obtained when the agent (b) included, as sealing reagent (b1), an alkalizing agent comprising at least one alkaline earth metal hydroxide. Suitable alkaline earth metal hydroxides include magnesium hydroxide, calcium hydroxide and barium hydroxide.

Satisfactory results were also obtained when the agent (b) included at least one alkali metal silicate and/or alkali metal metasilicate as sealing reagent (b1). Suitable alkali metal silicates include sodium silicate and potassium silicate. Suitable alkali metal metasilicates include sodium metasilicate and potassium metasilicate.

Satisfactory results were also obtained when the agent (b) included at least one alkali metal carbonate and/or alkaline earth metal carbonate as sealing reagent (b1). Suitable alkali metal carbonates include sodium carbonate and potassium carbonate. Suitable alkaline earth metal carbonates include magnesium carbonate and calcium carbonate.

Within the group of the sealing reagents (b1) in the form of an alkalizing agent, ammonia, $C_2$-$C_6$ alkanolaminenes, basic amino acids and alkali metal hydroxides have proved to be particularly suitable.

In the context of a further particularly preferred embodiment, the agent (b) comprises as sealing reagent (b1) at least one alkalizing agent selected from the group of ammonia, $C_2$-$C_6$ alkanolamines, basic amino acids and alkali metal hydroxides.

In another particularly preferred embodiment, the agent (b) comprises, as sealing reagent (b1), at least one alkalizing agent selected from the group of ammonia, 2-aminoethan-1-ol, 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, and/or potassium hydroxide.

The agent (b) comprises the alkalizing agent as a sealing reagent (b1) in a cosmetic carrier, preferably in an aqueous cosmetic carrier.

In this context, it has been found preferable if the agent (b) comprises—based on the total weight of the agent (b)—5.0 to 99.0% by weight, preferably 15.0 to 97.0% by weight, more preferably 25.0 to 97.0% by weight, still more preferably 35.0 to 97.0% by weight and very particularly preferably 45.0 to 97.0% by weight of water.

In the context of a further embodiment, the agent (b) comprises—based on the total weight of the agent (b)—5.0 to 99.0% by weight, preferably 15.0 to 97.0% by weight, more preferably 25.0 to 97.0% by weight, still more preferably 35.0 to 97.0% by weight and very particularly preferably 45.0 to 97.0% by weight of water.

The alkalizing agents included in the agent (b) exert an influence on the pH value of the agent (b). It was found that certain alkaline pH values have a beneficial effect on the dyeing performance achievable in the process and the fastness properties of the dyeing.

For this reason, it is preferred that the agent (b) comprising an alkalizing agent as sealing reagent (b1) has a pH of from 7.0 to 12.0, preferably from 7.5 to 11.5, more preferably from 8.0 to 11.0, and most preferably from 8.5 to 9.5.

The pH value can be measured using the usual methods known from the state of the art, such as pH measurement using glass electrodes via combination electrodes or using pH indicator paper.

In another very particularly preferred embodiment, the agent (b) comprises an alkalizing agent as sealing reagent (b1) and has a pH of from 7.0 to 12.0, preferably from 7.5 to 11.5, more preferably from 8.0 to 11.0 and most preferably from 8.5 to 9.5.

The pH values for the purposes of the present disclosure are pH values measured at a temperature of 22° C.

In a still further alternative embodiment, the sealing reagent (b1) comprises an acidifying agent.

Particularly preferably, the acidifying agent is selected from the group of inorganic acids, organic acids, and mixtures thereof.

Satisfactory results could be obtained when agent (b) comprises at least one inorganic acid as sealing reagent (b1). Suitable inorganic acids are, for example, phosphoric acid, sulfuric acid and/or hydrochloric acid, with sulfuric acid being particularly preferred.

In a further preferred embodiment, the agent (b) comprises, as sealing reagent (b1), at least one acidifying agent selected from the group of inorganic acids, which is preferably selected from the group of phosphoric acid, sulfuric acid, hydrochloric acid, and mixtures thereof.

In a further, even more preferred embodiment, the agent (b) comprises sulfuric acid as sealing reagent (b1).

Satisfactory results were also obtained when agent (b) included at least one organic acid as sealing reagent (b1). The organic acid is preferably selected from the group of formic acid, acetic acid, propionic acid, butyric acid, isobutyric acid, valeric acid, isovaleric acid, pivalic acid, oxalic acid, malonic acid, succinic acid, glutaric acid, glyceric acid, Glyoxylic acid, adipic acid, pimelic acid, corkic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluoylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-napthalenepentaacetic acid, malonaldehyde acid, 4-hydroxy-phthalamic acid, 1-pyrazolecarboxylic acid, gallic acid or propane tricarboxylic acid, glycolic acid, gluconic acid, lactic acid, maleic acid, ascorbic acid, malic acid, tartaric acid, citric acid and mixtures thereof.

In a further preferred embodiment, the agent (b) comprises as sealing reagent (b1) at least one acidifying agent selected from the group of organic acids, wherein the organic acid is preferably selected from the group of formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, corkic acid, azelaic acid, sebacic acid, propiolic acid, crotonic acid, isocrotonic acid, elaidic acid, Maleic acid, fumaric acid, muconic acid, citraconic acid, mesaconic acid, camphoric acid, benzoic acid, o,m,p-phthalic acid, naphthoic acid, toluoylic acid, hydratropasic acid, atropasic acid, cinnamic acid, isonicotinic acid, nicotinic acid, bicarbamic acid, 4,4'-dicyano-6,6'-binicotinic acid, 8-carbamoyloctanoic acid, 1,2,4-pentane tricarboxylic acid, 2-pyrrole carboxylic acid, 1,2,4,6,7-napthalene pentaacetic acid, malonaldehyde acid, 4-hydroxy-phthalamic acid, 1-pyrazole carboxylic acid, gallic acid or propane tricarboxylic acid, glycolic acid, gluconic acid, lactic acid, maleic acid, ascorbic acid, malic acid, tartaric acid, citric acid and mixtures thereof.

In a further, even more preferred embodiment, the agent (b) comprises acetic acid as sealing reagent (b1).

Also, suitable acidifiers include methanesulfonic acid and/or 1-hydroxyethane-1,1-diphosphonic acid.

Within the group of the above-mentioned sealing reagents (b1) in the form of an acidifying agent, sulfuric acid and/or acetic acid have proved to be particularly suitable.

In the context of a further particularly preferred embodiment, the agent (b) comprises as sealing reagent (b1) at least one acidifying agent selected from the group of sulfuric acid, acetic acid, and mixtures thereof.

The agent (b) comprises the acidifying agent as sealing reagent (b1) in a cosmetic carrier, preferably in an aqueous cosmetic carrier.

The acidifying agents included in the agent (b) exert an influence on the pH of the agent (b). It was found that acidic pH values also have a beneficial effect on the dyeing performance achievable in the process and the fastness properties of the dyeing.

For this reason, it is preferred that the agent (b) comprising an acidifying agent as sealing reagent (b1) has a pH of from 2.0 to 6.5, preferably from 3.0 to 6.0, more preferably from 4.0 to 6.0, and most preferably from 4.5 to 5.5.

The pH value can be measured using the usual methods known from the state of the art, such as pH measurement using glass electrodes via combination electrodes or using pH indicator paper.

In another very particularly preferred embodiment, the agent (b) comprises an acidifying agent as sealing reagent (b1) and has a pH of from 2.0 to 6.5, preferably from 3.0 to 6.0, more preferably from 4.0 to 6.0, and most preferably from 4.5 to 5.5.

The pH values for the purposes of the present disclosure are pH values measured at a temperature of 22° C.

Other Ingredients in Agents (a) and (b)

The agents (a) and (b) described above may also contain one or more optional ingredients. However, it is essential to the present disclosure that at least one of the agents (a) and (b) further comprises at least one colorant compound selected from the group of pigments and/or direct dyes.

It may be preferred that the agent (a), in addition to the at least one organic silicon compound selected from the group of silanes having one, two or three silicon atoms (a1) and the at least one phosphoric acid ester (a2), further comprises at least one coloring compound selected from the group of pigments and/or direct dyes.

Alternatively, it may be preferred that the agent (b) further comprises, in addition to the sealing reagent (b1), at least one colorant compound selected from the group of pigments and/or direct dyes.

In an equally preferred embodiment of the process, the agent (a) and the agent (b) each further comprise at least one colorant compound selected from the group of pigments and/or direct dyes.

Irrespective of agent (a) and/or (b), the use of pigments has proved to be particularly preferred in this context.

In another very particularly preferred embodiment, the agent (a) and/or the agent (b) further comprises at least one color-imparting compound selected from the group of pigments.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A beaker glass is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable pigments can be of inorganic and/or organic origin.

In a preferred embodiment, the agent (a) and/or the agent (b) further comprises at least one colorant compound selected from the group of inorganic and/or organic pigments.

Preferred pigments are selected from synthetic or natural inorganic pigments. Inorganic pigments of natural origin can be produced, for example, from chalk, ochre, umber, green earth, fired Terra di Siena or graphite. Furthermore, black pigments such as iron oxide black, colored pigments such as ultramarine or iron oxide red, and fluorescent or phosphorescent pigments can be used as inorganic pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Particularly preferred pigments are black iron oxide (CI 77499), yellow iron oxide (CI 77492), red and brown iron oxide (CI 77491), manganese violet (CI 77742), ultramarines (sodium aluminum sulfosilicates, CI77007, Pigment Blue 29), chromium oxide hydrate (CI77289), iron blue (ferric ferrocyanide, CI77510) and/or carmine (cochineal).

Also particularly preferred pigments are colored pearlescent pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

Accordingly, in a preferred process the agent (a) and/or the agent (b) further comprises at least one colorant compound selected from the group of pigments selected from the group of colored metal oxides, metal hydroxides, metal oxide hydrates, silicates, metal sulfides, complex metal cyanides, metal sulfates, bronze pigments and/or colored pigments based on natural or synthetic mica coated with at least one metal oxide and/or a metal oxychloride.

In a further preferred embodiment, the agent (a) and/or the agent (b) comprises at least one colorant compound from the group of pigments selected from pigments based on natural or synthetic mica which are reacted with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

In a further preferred embodiment, the agent (a) comprises a coloring compound selected from the group of iron oxide pigments. Within this embodiment, it is particularly preferred that the iron oxide pigment is selected from the group of black iron oxide (CI 77499), yellow iron oxide (CI 77492), red iron oxide (CI 77491) and mixtures thereof and has a particle diameter in the range of 100 to 1,000 nm, more preferably 150 nm 700 nm.

In this context, it has surprisingly been found that the use of a phosphoric acid ester (a2) comprising an ester with the INCI designation:Ceteth-20 phosphates in combination with a coloring compound comprising a pigment from the group of iron oxide pigments with a particle diameter in the range from 100 to 1000 nm leads to particularly intense and uniform colorations.

A preferred suitable pigment based on synthetic mica is, for example, Timiron SynWhite Satin from Merck.

Other suitable pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

Examples of particularly suitable pigments are commercially available under the trade names Rona®, Colorona®, Xirona®, Dichrona® and Timiron® from Merck, Ariabel® and Unipure® from Sensient, Prestige® or SynCrystal from Eckart Cosmetic Colors, Flamenco®, Cellini®, Cloisonné®, Duocrome®, Gemtone®, Timica®, MultiReflections, Chione from BASF SE and Sunshine® from Sunstar.

Very particularly preferred pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D & C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, Mica, CI 77891 (Titanium dioxide), Silica, CI 77491 (Iron oxides), Tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (Iron oxides), Mica, CI 77891 (Titanium dioxide)

Colorona Bright Gold, Merck, Mica, CI 77891 (Titanium dioxide), CI 77491(Iron oxides)

Colorona Blackstar Gold, Merck, MICA, CI 77499 (IRON OXIDES)

Colorona® SynCopper, Merck, Synthetic Fluorophlogopite (and) Iron Oxides

Colorona® SynBronze, Merck, Synthetic Fluorophlogopite (and) Iron Oxides

Further particularly preferred pigments with the trade name Xirona® are, for example:

Xirona Golden Sky, Merck, Silica, CI 77891 (Titanium Dioxide), Tin Oxide

Xirona Caribbean Blue, Merck, Mica, CI 77891 (Titanium Dioxide), Silica, Tin Oxide Xirona Kiwi Rose, Merck, Silica, CI 77891 (Titanium Dioxide), Tin Oxide Xirona Magic Mauve, Merck, Silica, CI 77891 (Titanium Dioxide), Tin Oxide.

Xirona® Le Rouge, Merck, Iron Oxides (and) Silica

In addition, particularly preferred pigments with the trade name Unipure® are, for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

Also particularly preferred pigments with the trade name Flamenco® are, for example:

Flamenco® Summit Turquoise T30D, BASF, Titanium Dioxide (and) Mica

Flamenco® Super Violet 530Z, BASF, Mica (and) Titanium Dioxide

In a further embodiment, the agent (a) and/or agent (b) used in the process may also comprise one or more colorant compounds from the group of organic pigments.

The organic pigments are correspondingly insoluble organic dyes or colorants which may be selected, for example, from the group of nitroso, nitro, azo, xanthene, anthraquinone, isoindolinone, isoindoline, quinacridone, perinone, perylene, diketopyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the agent (a) and/or the agent (b) comprises at least one colorant compound from the group of organic pigments selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The organic pigment can also be a color lacquer. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

In a further preferred embodiment, the agent (a) comprises a coloring compound selected from the group of organic pigments. Within this embodiment, it is particularly preferred that the organic pigment has a particle diameter in the range of 100 to 1,000 nm, more preferably 150 nm 700 nm.

In this context, it has been surprisingly shown that the use of a phosphoric acid ester (a2) comprising an ester with the INCI designation Ceteth-20 phosphates in combination with a coloring compound comprising an organic pigment with a particle diameter in the range of 100 to 1,000 nm leads to particularly intense and uniform colorations.

Also, suitable colorant compounds from the group of pigments are inorganic and/or organic pigments modified with a polymer. The polymer modification can, for example, increase the affinity of the pigments to the respective material of the at least one layer.

In agent (a) and/or agent (b) it is also possible to use so-called metal effect pigments as colorant.

In particular, the metal effect pigments may include pigments based on a lamellar substrate platelet, pigments based on lenticular substrate platelets, and/or pigments based on substrate platelets comprising "vacuum metallized pigments" (VMP). In these metal effect pigments, the substrate platelets comprise a metal, preferably aluminum, or an alloy. Metal substrate platelet-based metal effect pigments preferably have a coating which, among other things, acts as a protective layer.

Suitable metallic effect pigments include, for example, the pigments Alegrace® Marvelous, Alegrace© Gorgeous or Alegrace® Aurous from Schlenk Metallic Pigments.

Also, suitable metal effect pigments are the aluminum-based pigments of the SILVERDREAM series, and the pigments based on aluminum or on copper/zinc-comprising metal alloys of the VISIONAIRE series from Eckart.

Surprisingly, the use of phosphoric acid esters (a2), comprising an ester of orthophosphoric acid with a branched aliphatic alcohol having 11 to 14 carbon atoms, in the process as contemplated herein has been shown to improve the elevator of aluminum-based pigments. As a result, the colorations obtained were particularly uniform and intense.

Likewise suitable effect pigments are based on substrate platelets of natural or artificial mica, which are preferably coated with at least one metal oxide (hydrate) layer. Such pigments are available, for example, under the name Timiron SynWhite Satin from Merck.

Due to their excellent light and temperature stability, the use of the above pigments in agent (a) and/or (b) is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D_{50}$ of 1 to 50 µm, preferably 5 to 45 µm, preferably 10 to 40 µm, 14 to 30 µm. The average particle size $D_{50}$, for example, can be determined using dynamic light scattering (DLS).

In a further preferred embodiment, the agent (a)—based on the total weight of the agent (a)—further comprises one or more color-imparting compound(s) in the form of pigments in a total amount of from 0.01 to 10 wt. %, preferably from 0.1 to 8 wt. %, more preferably from 0.2 to 6 wt. % and most preferably from 0.5 to 4.5 wt. %.

In a further, likewise preferred embodiment, the agent (b)—based on the total weight of the agent (b)—further comprises one or more color-imparting compound(s) in the form of pigments in a total amount of from 0.01 to 10 wt. %, preferably from 0.1 to 8 wt. %, more preferably from 0.2 to 6 wt. % and very particularly preferably from 0.5 to 4.5 wt. %.

As colorant compound(s), the agents (a) and/or agents (b) used in the process may also contain one or more direct dyes.

Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1 g/L.

Direct dyes can be divided into anionic, cationic, and non-ionic direct dyes.

In a further preferred embodiment, the agent (a) and/or the agent (b) further comprises as coloring compound at least one anionic, cationic and/or nonionic direct dye.

In a further preferred embodiment, the agent (a) and/or the agent (b) further comprises at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In the course of the work leading to the present disclosure, it has been found that dyeing of particularly high color intensity can be produced with agents (a) and/or (b) comprising at least one anionic direct dye.

In an explicitly quite particularly preferred embodiment, the agent (a) and/or the agent (b) further comprises at least one anionic direct dye as a coloring compound.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—OO$^-$, —SO$_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. The acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In the context of one embodiment, a process for dyeing keratinous material is thus preferred, wherein the agent (a) and/or the agent (b) further comprises at least one anionic direct dye as coloring compound, which is selected from the group of the nitrophenylenediamines, the nitroaminophenols, the azo dyes, the anthraquinone dyes, the triarylmethane dyes, the xanthene dyes, the rhodamine dyes, the oxazine dyes and/or the indophenol dyes, the dyes from the above-mentioned group each comprising at least one carboxylic acid group (—COOH), a sodium carboxylate group (—COONa), a potassium carboxylate group (—COOK), a sulfonic acid group (—$SO_3H$), a sodium sulfonate group (—$SO_3Na$) and/or a potassium sulfonate group (—$SO_3K$).

For example, one or more compounds from the following group can be selected as particularly well suited acid dyes: Acid Yellow 1 (D & C Yellow 7, Citronin A, Ext. D & C Yellow No. 7, Japan Yellow 403, CI 10316, COLIPA no B001), Acid Yellow 3 (COLIPA no: C 54, D & C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF), Tartrazine, Food Yellow 4, Japan Yellow 4, FD & C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D & C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real red D, FD & C Red Nr. 2, Food Red 9, Naphthol red S), Acid Red 33 (Red 33, Fuchsia Red, D & C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C53, CI 45410), Acid Red 95 (CI 45425, Erythrosine, Simacid Erythrosine Y), Acid Red 184 (CI 15685), Acid Red 195, Acid Violet 43 (Jarocol Violet 43, Ext. D & C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D & C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D & C Yellow 8, D & C Green 5, D & C Orange 10, D & C Orange 11, D & C Red 21, D & C Red 27, D & C Red 33, D & C Violet 2 and/or D & C Brown 1.

For example, the water solubility of anionic direct dyes can be determined in the following way. 0.1 g of the anionic direct dye is placed in a beaker. An agitator is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a very high-water solubility of more than 20 wt. %.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a water solubility of greater than 20 wt. % (25° C.).

in a very particularly preferred process the agent (a) and/or the agent (b) further comprises at least one colorant compound selected from the group of anionic direct dyes, which is selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D & C Yellow 8, D & C Green 5, D & C Orange 10, D & C Orange 11, D & C Red 21, D & C Red 27, D & C Red 33, D & C Violet 2 and/or D & C Brown 1.

The direct dye(s), in particular the anionic direct dyes, can be used in different amounts in the agent (a) and/or the agent (b) depending on the desired color intensity. Particularly good results were obtained when the agent (a) and/or the agent (b)—in each case based on its total weight—also comprises one or more direct dyes as colorant compound in a total amount of from 0.01 to 10 wt. %, preferably from 0.1 to 8 wt. %, more preferably from 0.2 to 6 wt. % and very particularly preferably from 0.5 to 4.5 wt. %.

In a further preferred embodiment, the agent (a) and/or the agent—based on the total weight of the agent (a) and/or the agent (b)—further comprises one or more direct dyes as colorant compound in a total amount of from 0.01 to 10 wt. %, preferably from 0.1 to 8 wt. %, more preferably from 0.2 to 6 wt. % and most preferably from 0.5 to 4.5 wt. %.

Preferred embodiments of the process with respect to the colorant compounds are disclosed below:
1. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one inorganic pigment selected from the group of colored metal oxides, metal hydroxides, metal oxide hydrates, silicates, metal sulfides, complex metal cyanides, metal sulfates, bronze pigments, and mixtures thereof,
application of an agent (b) to the keratinous material, wherein the agent (b) comprises:
(b1) at least one sealing reagent.
2. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one inorganic pigment selected from the group of colored metal oxides, metal hydroxides, metal oxide hydrates, silicates, metal sulfides, complex metal cyanides, metal sulfates, bronze pigments and mixtures thereof and at least one pigment selected from the group of pigments based on a lamellar metallic substrate platelet, pigments based on a lenticular metallic substrate platelet, pigments based on a metallic substrate platelet comprising a vacuum metallized pigment (VMP) and mixtures thereof,
application of an agent (b) to the keratinous material, wherein the agent (b) comprises:
(b1) at least one sealing reagent.
3. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one inorganic pigment selected from the group of colored metal oxides, metal hydroxides, metal oxide hydrates, silicates, metal sulfides, complex metal cyanides, metal sulfates, bronze pigments, and mixtures thereof, and at least one pigment comprising α) a substrate platelet comprising mica, and β) a coating comprising at least a first metal oxide (hydrate) layer comprising $TiO_2$, $SnO_2$ and/or iron oxide(s),
application of an agent (b) to the keratinous material, wherein the agent (b) comprises:
(b1) at least one sealing reagent.
4. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one inorganic pigment selected from the group of colored metal oxides, metal hydroxides, metal oxide hydrates, silicates, metal sulfides, complex metal cyanides, metal sulfates, bronze pigments, and mixtures thereof,
application of an agent (b) to the keratinous material, wherein the agent (b) comprises:
(b1) at least one sealant reagent comprising a film-forming polymer, and
at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.
5. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one inorganic pigment selected from the group of colored metal oxides, metal hydroxides, metal oxide hydrates, silicates, metal sulfides, complex metal cyanides, metal sulfates, bronze pigments, and mixtures thereof,
application of an agent (b) to the keratinous material, wherein the agent (b) comprises:
(b1) at least one sealant reagent comprising a film-forming polymer, and at least one colorant compound comprising a pigment comprising α) a substrate platelet comprising mica, and β) a coating comprising at least a first metal oxide (hydrate) layer comprising $TiO_2$, $SnO_2$ and/or iron oxide(s).

6. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one inorganic pigment selected from the group of colored metal oxides, metal hydroxides, metal oxide hydrates, silicates, metal sulfides, complex metal cyanides, metal sulfates, bronze pigments, and mixtures thereof,
application of an agent (b) to the keratinous material, wherein the agent (b) comprises:
(b1) at least one sealant reagent comprising a film-forming polymer, and
at least one colorant compound comprising a pigment comprising α) a substrate platelet comprising borosilicate glass, and β) a coating comprising at least a first metal oxide (hydrate) layer comprising TiO₂, SnO₂, SiO₂, and/or iron oxide(s).

7. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
application of an agent (b) to the keratinous material, wherein the agent (b) comprises:
(b1) at least one sealing reagent.

8. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one coloring compound comprising at least one organic pigment selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment selected from the group of pigments based on a lamellar, metallic substrate platelet-based pigments, lenticular metallic substrate platelet-based pigments, metallic substrate platelet-based pigments comprising a vacuum metallized pigment (VMP), and mixtures thereof,
application of an agent (b) to the keratinous material, wherein the agent (b) comprises:
(b1) at least one sealing reagent.

9. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one organic pigment selected from the group of carmine, quinacridone, phthalocyanine, sorghum, blue pigments having the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment comprising α) a substrate platelet comprising mica, and β) a coating comprising at least a first metal oxide (hydrate) layer comprising TiO₂, SnO₂ and/or iron oxide(s),
application of an agent (b) to the keratinous material, wherein the agent (b) comprises:
(b1) at least one sealing reagent.

10. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
application of an agent (b) to the keratinous material, wherein the agent (b) comprises:
(b1) at least one sealant reagent comprising a film-forming polymer, and at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.

11. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
application of an agent (b) to the keratinous material, wherein the agent (b) comprises:
(b1) at least one sealant reagent comprising a film-forming polymer, and at least one colorant compound comprising a pigment comprising α) a substrate platelet comprising mica, and β) a coating comprising at least a first metal oxide (hydrate) layer comprising $TiO_2$, $SnO_2$ and/or iron oxide(s).

12. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one phosphoric acid ester and
at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
application of an agent (b) to the keratinous material, wherein the agent (b) comprises:
(b1) at least one sealant reagent comprising a film-forming polymer, and
at least one colorant compound comprising a pigment comprising α) a substrate platelet comprising borosilicate glass, and β) a coating comprising at least a first metal oxide (hydrate) layer comprising $TiO_2$, $SnO_2$, $SiO_2$, and/or iron oxide(s).

13. A process for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms, and
(a2) at least one phosphoric acid ester
application of an agent (b) to the keratinous material, wherein the agent (b) comprises:
(b1) at least one sealant reagent comprising a film-forming polymer, and
at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.

In the embodiment according to item 13, it may be further preferred that the agent (b) further comprises at least one phosphoric acid ester.

The agents may also contain one or more surfactants. The term surfactants refer to surface-active substances. A distinction is made between anionic surfactants comprising a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$— or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI designation cocamidopropyl betaine.

Ampholytic surfactants are surface-active compounds which, in addition to a $C_8$-$C_{24}$ alkyl or acyl group in the molecule, contain at least one free amino group and at least one —COOH or —$SO_3$H group and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkyl-betaines, alkylamidobetaines, amino propionates, aminoglycinate, imidazoliniumbetaines and sulfobetaines.

Particularly preferred ampholytic surfactants are N-cocosalkylaminopropionate, cocosacylaminoethylaminopropionate and $C_{12}$-$C_{18}$-acylsarcosine.

The agents may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with suitable properties are also obtained if they contain as non-ionic surfactants fatty acid esters of ethoxylated glycerol reacted with at least 2 mol ethylene oxide.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually of a hydrocarbon backbone (e.g., of one or two linear or branched alkyl chains) and the positive charge(s) being in the hydrophilic head group. Examples of cationic surfactants are quaternary ammonium compounds which may carry one or two alkyl chains with a chain length of 8 to 28 carbon atoms as hydrophobic radicals, quaternary phosphonium salts substituted by one or more alkyl chains having a chain length of 8 to 28 carbon atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the agent (a) and/or the agent (b) may/can also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule. Particularly suitable anionic surfactants include sulfated vegetable oils, especially sulfated castor oil ("Turkish red oil").

The anionic surfactants are used in a total quantity of 0.1 to 45 wt. %, preferably 1 to 30 wt. % and most preferably 1 to 15 wt. %—based on the total weight of the respective agent.

Agent (a) and/or agent (b) may further comprise a matting agent. Suitable matting agents include, for example, (modified) starches, waxes, talc and/or (modified) silicic acids. The amount of matting agent is preferably between 0.1 and 10 wt. % based on the total amount of agent (a) or agent (b). Preferably, agent (a) comprises a matting agent.

The agent (a) and/or the agent (b) may further comprise a thickening agent.

When using agents (a) and/or (b), they must not be too thin and drip off the keratin material. For this reason, it may be preferred that the agent (a) and/or (b) comprises a thickening agent.

In the context of one embodiment, a process for dyeing keratinous material is thus preferred, wherein the agent (a) and/or the agent (b) further comprises a thickening agent.

Suitable thickeners include, for example, chemically modified celluloses, such as propyl cellulose, methyl ethyl cellulose, carboxymethyl cellulose, hydroxyethyl cellulose, methyl hydroxyethyl cellulose, ethyl hydroxyethyl cellulose, hydroxypropyl cellulose, hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethylhydroxyethylcellulose, methlylsulfoethylcellulose and/or ethylsulfoethylcellulose.

In a preferred embodiment, the agent (a) and/or the agent (b) further comprises a thickening agent selected from the group of propylcellulose, methyl ethylcellulose, carboxymethylcellulose, hydroxyethylcellulose, methylhydroxyethylcellulose, ethylhydroxyethylcellulose, hydroxypropylcellulose, hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethylhydroxyethylcellulose, methlylsulfoethylcellulose, ethylsulfoethylcellulose, and mixtures thereof Particularly suitable thickeners are selected from hydroxyethyl cellulose, hydroxypropyl cellulose, hydroxypropyl methyl cellulose and mixtures thereof.

In a particularly preferred embodiment, the agent (a) and/or the agent (b) further comprises a thickening agent selected from the group of hydroxyethylcellulose, hydroxypropylcellulose, hydroxypropylmethylcellulose and mixtures thereof.

The amount of thickener is preferably between 0.1 and 10 wt. %, in each case based on the total amount of agent (a) and/or agent (b).

It may be further preferred that the agent (a) further comprises at least one $C_1$-$C_{10}$ alcohol.

The $C_1$-$C_{10}$ alcohol is preferably a $C_1$-$C_{10}$ aliphatic alcohol, which may be linear or branched and saturated or unsaturated.

Preferred $C_1$-$C_{10}$ alcohols are selected from the group of methanol, ethanol, 1-propanol, 2-propanol, 1-butanol, 2-butanol, 2-methylpropan-1-ol, 2-methylpropan-1-ol (tert. Butanol), 1-pentanol, 2-pentanol, 3-pentanol, 3-methylbutan-1-ol, 2-methylbutan-1-ol, 2,2-dimethylpropan-1-ol, 3-methylbutan-2-ol, 2-methylbutan-2-ol, 1-hexanol, 2-hexanol, 3-hexanol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol, 2-ethylbutan-1-ol, 1-heptanol, 2-heptanol, 3-heptanol, 4-heptanol, 1-octanol, 2-octanol, 1-nonanol, 1-decanol, 2-methylhexan-2-ol, 2-methylheptan-2-ol, 3-methyl-3-pentanol, and mixtures thereof.

Of the $C_1$-$C_{10}$ alcohols, the agent (a) preferably comprises at least one $C_1$-$C_{10}$ alcohol selected from the group of methanol, ethanol, 1-propanol, 2-propanol, 1-butanol, 2-butanol, 2-methylpropan-1-ol, 2-methylpropan-1-ol (tert-butanol), and mixtures thereof In a highly preferred embodiment, the agent (a) further comprises at least one $C_1$-$C_{10}$ alcohol selected from the group of ethanol, 2-propanol, and mixtures thereof.

It may also be preferred that the agent (a) further comprises at least one diol.

It may also be preferred that the pigment suspension further comprises at least one diol. An aliphatic diol is also known as a glycol.

Preferred diols are $C_2$-$C_9$ alkanols with two hydroxyl groups and polyethylene glycols with 3 to 20 ethylene oxide units. The agent (a) may further comprise at least one $C_2$-$C_9$ alkanol having two hydroxyl groups or at least one water-soluble polyethylene glycol having 3 to 20 ethylene oxide units or mixtures of at least one $C_2$-$C_9$ alkanol having two hydroxyl groups and at least one water-soluble polyethylene glycol having 3 to 20 ethylene oxide units.

Preferably, the $C_2$-$C_9$ alkanols with two hydroxyl groups are selected from ethylene glycol, 1,2-propylene glycol, 1,3-propylene glycol, 2-methyl-1,3-propanediol, 1,2-butylene glycol, 1,3-butylene glycol, 1,4-butylene glycol, 1,2-pentanediol, 1,5-pentanediol, 1,2-hexanediol, 1,6-hexanediol, 1,2-octanediol, 1,8-octanediol, cis-1,4-dimethylolcyclohexane, trans-1,4-dimethylolcyclohexane, any isomeric mixtures of cis- and trans-1,4-dimethylolcyclohexane, and mixtures of these diols. Also, suitable diols are diethylene glycol, dipropylene glycol and/or PPG-10 butanediol (INCI). Suitable water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, and mixtures thereof. PEG-9 stands for a polyethylene glycol with 9 ethylene oxide units. This has an average molecular weight of 400 daltons and is also referred to as from PEG 400.

Of said diols, agent (a) preferably comprises at least one diol selected from the group of ethylene glycol, 1,2-propylene glycol, 1,3-propylene glycol, 1,2-butylene glycol, 1,3-butylene glycol, 1,4-butylene glycol, 1,2-pentanediol, 1,5-pentanediol, 1,2-hexanediol, 1,6-hexanediol, PEG-8, PEG-9, and PPG-10 butanediol (INCI).

In a highly preferred embodiment, the agent (a) further comprises at least one diol selected from the group of ethylene glycol, 1,2-propylene glycol, 1,3-propylene glycol, PEG-9, and mixtures thereof.

The agents may also contain other active ingredients, auxiliaries and additives, such as solvents; fatty ingredients such as $C_8$-$C_{30}$ fatty acid triglycerides, $C_8$-$C_{30}$ fatty acid monoglycerides, $C_8$-$C_{30}$ fatty acid diglycerides and/or the hydrocarbons; structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosene; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The specialist will make the selection of these other substances according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Process for Dyeing Keratinous Materials

In the procedure as contemplated herein, agents (a) and (b) are applied to the keratinous materials, to human hair. Thus, agents (a) and (b) are the ready-to-use agents. The agents (a) and (b) are different.

In principle, agents (a) and (b) can be applied simultaneously or successively, whereby successive application is preferred.

The best results were obtained when agent (a) was first applied to the keratinous materials in a first step and agent (b) was applied in a second step.

Quite particularly preferred, therefore, is a process for treating keratinous material, for coloring keratinous material, in particular human hair, comprising the following steps in the order indicated:

in a first step, applying an agent (a) to the keratinous material, the agent comprising (a):
(a1) at least one organic silicon compound selected from the group of silanes having one, two or three silicon atoms, and
(a2) at least one phosphoric acid ester In a second step, applying an agent (b) to the keratinous material, the agent comprising (b):
(b1) at least one sealing reagent,
wherein at least one of the agents (a) and (b) further comprises at least one colorant compound selected from the group of pigments and/or direct dyes.

Moreover, to impart a high leaching resistance to the dyed keratinous material over a longer period, agents (a) and (b) are particularly preferably applied within the same dyeing process, which means that there is a period of a maximum of several hours between the application of agents (a) and (b).

In a further preferred embodiment, agent (a) is applied first and agent (b) is applied thereafter, the period between the application of agents (a) and (b) being at most 24 hours, preferably at most 12 hours and particularly preferably at most 6 hours.

A distinguishing feature of the agent (a) is its content of at least one reactive organic silicon compound (a1). The reactive organic silicon compound(s) (a1) undergoes an oligomerization or polymerization reaction and thus functionalizes the hair surface as soon as it meets it. In this way, a first, film is formed. In the second step of the process, a second agent (b) is now applied to the hair. During the application of the agent (b) comprising at least one film-forming polymer as sealing reagent (b1), the latter interacts with the silane film and is thus bound to the keratinous materials. During the application of agent (b) comprising at least one alkalizing agent or acidifying agent as sealing reagent (b1), the formation of the silane film is positively influenced. The desired coloring of the keratinous material is achieved by employing the coloring compound in agent (a) and/or in agent (b). The coloration can be achieved by a colored silane film (the colorant compound is only in agent (a)), by a colored polymer film (the coloring compound is only in agent (b) and this comprises a film-forming polymer as sealing reagent (b1)) or by a colored silane film and by a colored polymer film (agents (a) and (b) each contain at least one coloring compound and agent (b) comprises a film-forming polymer as sealing reagent (b1)).

In the context of a further embodiment, a method is very particularly preferred, comprising the following steps in the order indicated.
(1) Application of the agent (a) on the keratinous material,
(2) Allow the agent (a) to act for a period of 10 seconds to 10 minutes, preferably from 10 seconds to 5 minutes,
(3) if necessary, rinse the keratinous material with water,
(4) Application of agent (b) on the keratinous material,
(5) Allowing the agent (b) to act for a period of 30 seconds to 30 minutes, preferably from 30 seconds to 10 minutes,
(6) Rinse the keratinous material with water.

The rinsing of the keratinous material with water in steps (3) and (6) of the process is understood, as contemplated herein, to mean that only water is used for the rinsing process, without any other agents other than agents (a) and (b).

In step (1), agent (a) is first applied to the keratinous materials, in particular human hair.

After application, the agent (a) is left to act on the keratinous materials. In this context, application times from 10 seconds to 10 minutes, preferably from 20 seconds to 5 minutes and especially preferably from 30 seconds to 2 minutes on the hair have proven to be particularly beneficial.

In a preferred embodiment of the process, the agent (a) can now be rinsed from the keratinic materials before the agent (b) is applied to the hair in the subsequent step.

Stains with equally good wash fastnesses were obtained when agent (b) was applied to the keratinous materials that were still exposed to agent (a).

In step (4), agent (b) is now applied to the keratinous materials. After application, let the agent (b) act on the hair.

Even with a short contact time of the agent (b), the process allows the production of dyeing with particularly good intensity and wash fastness. Application times from 10 seconds to 10 minutes, preferably from 20 seconds to 5 minutes and most preferably from 30 seconds to 3 minutes on the hair have proven to be particularly beneficial.

In step (6), the agent (b) (and any agent (a) still present) is now rinsed out of the keratinous material with water.

In this embodiment, the sequence of steps (1) to (6) preferably takes place within 24 hours.

Agent (a) comprises, with the organic silicon compound(s), a class of highly reactive compounds that can undergo hydrolysis or oligomerization and/or polymerization when used. As a result of their high reactivity, these organic silicon compounds form a film on the keratinous material.

To avoid premature oligomerization or polymerization, it is of considerable advantage to the user to prepare the ready-to-use agent (a) only shortly before application.

In yet another embodiment, preferred is a method comprising the following steps in the order indicated.
(1) Preparation of an agent (a) by mixing a first agent (a') and a second agent (a"), wherein
the first agent (a') comprises at least one organic silicon compound (a1) from the group of silanes having one, two or three silicon atoms, the second agent (a") comprises at least one phosphoric acid ester (a2) and at least one colorant compound selected from the group of pigments and/or direct dyes,
(2) Application of the agent (a) on the keratinous material,
(3) Allow the agent (a) to act for a period of 10 seconds to 10 minutes, preferably from 10 seconds to 5 minutes,
(4) if necessary, rinse the keratinous material with water,
(5) Application of agent (b) on the keratinous material,
(6) Allowing the agent (b) to act for a period of 30 seconds to 30 minutes, preferably from 30 seconds to 10 minutes,
(7) Rinse the keratinous material with water.

The user may first stir or shake the agent (a') comprising the organic silicon compound(s) (a1) with the agent (a").

To be able to provide a formulation that is as stable as possible in storage, the agent (a') itself is preferably formulated to be low in water or water-free.

In a preferred embodiment, the agent (a')—based on the total weight of the agent (a')—comprises a water content of from 0.001 to 10 wt. %, preferably from 0.5 to 9 wt. %, more preferably from 1 to 8 wt. % and very particularly preferably from 1.5 to 7 wt. %.

In the context of a further embodiment, therefore, a process may be preferred comprising the following steps in the order indicated.
(1) Preparation of an agent (a) by mixing a first agent (a'), a second agent (a") and a third agent (a'"), wherein
the first agent (a') comprises at least one organic silicon compound (a1) from the group of silanes having one, two or three silicon atoms,
the second agent (a") comprises at least one phosphoric acid ester (a2) and at least one colorant compound selected from the group of pigments and/or direct dyes, and the third agent (a'") comprises at least 30 wt. % water, based on the total weight of agent (a'"), and optionally at least one colorant compound from the group of pigments and/or direct dyes,
(2) Application of the agent (a) on the keratinous material,
(3) Allow the agent (a) to act for a period of 10 seconds to 10 minutes, preferably from 10 seconds to 5 minutes,
(4) if necessary, rinse the keratinous material with water,
(5) Application of agent (b) on the keratinous material,
(6) Allowing the agent (b) to act for a period of 30 seconds to 30 minutes, preferably from 30 seconds to 10 minutes,
(7) Rinse the keratinous material with water.

Within this embodiment, the ready-to-use agent (a) is prepared by mixing agents (a'), (a") and (a'").

For example, the user may first mix or shake the agent (a') comprising the organic silicon compound(s) (a1) with the agent (a") and the water-comprising agent (a'"). The user can now apply this mixture of (a'), (a") and (a'") to the keratinous materials—either immediately after its preparation or after a short reaction time of 10 seconds to 20 minutes. Afterwards, the user can apply agent (b) as described above.

Alternatively, the user can first mix or shake the agent (a") and the water-comprising agent (a'") and then mix the resulting mixture with agent (a') comprising the organic silicon compound(s) (a1). This mixture of (a'), (a") and (e) can be applied to the keratinous materials by the user—either immediately after its preparation or after a short reaction time of 10 seconds to 20 minutes. Afterwards, the user can apply agent (b) as described above.

The agent (a") and/or the agent (a'") may/could further comprise a thickening agent. Within this embodiment, it is preferred that the agent (a") comprises a thickening agent selected from the group of hydroxyethylcellulose, hydroxypropylcellulose, hydroxypropylmethylcellulose, and mixtures thereof.

In the case where the agent (b) comprises at least one colorant compound from the group of pigments and/or direct dyes, it may also be preferred to prepare the ready-to-use agent (b) by mixing two agents (b') and (b"). In this embodiment, the agent (b') comprises the sealing reagent (b1) and the agent (b") comprises the at least one colorant compound selected from the group of pigments and/or direct dyes.

Multi-Component Packaging Unit (Kit-of-Parts)

To increase user convenience, the user is preferably provided with all the necessary agents in the form of a multi-component packaging unit (kit-of-parts).

A second subject of the present disclosure is therefore a multi-component packaging unit (kit-of-parts) for coloring keratinous material, comprehensively packaged separately from one another
- a first container comprising an agent (a'), wherein the agent comprises (a'):
  - (a1) at least one organic silicon compound selected from the group of silanes having one, two or three silicon atoms,
- a second container comprising an agent (a"), wherein the agent comprises (a"):
  - (a2) at least one phosphoric acid ester and
- a third container comprising an agent (b), wherein the agent comprises (b):
  - (b1) at least one sealing reagent,
- where the components (a1), (a2) and (b1) have been disclosed in detail above, and at least one of the agents (a") and (b) further comprises at least one colorant compound selected from the group of pigments and/or direct dyes.

Another embodiment of the present disclosure is a multi-component packaging unit (kit-of-parts) for dyeing keratinous material, comprising separately prepared
- a first container comprising an agent (a'), wherein the agent comprises (a'):
  - (a1) at least one organic silicon compound selected from the group of silanes having one, two or three silicon atoms,
- a second container comprising an agent (a"), wherein the agent comprises (a"):
  - (a2) at least one phosphoric acid ester,
- a third container comprising an agent (a"'), said agent (a"') comprising:
  - at least 30 wt. %, based on the total weight of agent (a"'), of water; and
- a fourth container comprising agent (b), wherein the agent comprises (b):
  - (b1) at least one sealing reagent,
- where the components (a1), (a2) and (b1) have been disclosed in detail above, and at least one of the agents (a"), (a"') and (b) further comprises at least one colorant compound selected from the group of pigments and/or direct dyes.

The organic silicon compounds (a1) from the group of silanes with one, two or three silicon atoms included in the agent (a') of the kits correspond to the organic silicon compounds (a1) that were also used in the agent (a) of the previously described process.

The phosphoric acid ester (a2) included in the agent (a") of the kits corresponds to the phosphoric acid ester (a2) that was also used in the agent (a) of the process described above.

The sealing reagent (b1) included in the agent (b) of the kits corresponds to sealing reagent (b1) that was also used in the agent (b) of the process described previously.

In the context of a further embodiment, a multi-component packaging unit (kit-of-parts) for coloring keratinic material is preferably packaged separately from one another
- a first container comprising an agent (a'), wherein the agent comprises (a'):
  - at least one organic silicon compound (a1) from the group of silanes having one, two or three silicon atoms,
- a second container comprising an agent (a"), wherein the agent comprises (a"):
  - (a2) at least one phosphoric acid ester,
- a third container comprising an agent (a"'), said agent (a"') comprising:
  - at least 30 wt. %, based on the total weight of agent (a"'), of water; and
- a fourth container comprising agent (b), wherein the agent comprises (b):
  - (b1) at least one sealing reagent comprising a film-forming polymer, and further a coloring compound selected from the group of pigments and/or direct dyes,
- wherein the components (a1), (a2) and (b1) have been disclosed in detail above.

In the context of still another embodiment, preferred is a multi-component packaging unit (kit-of-parts) for dyeing keratinous material, comprising separately prepared
- a first container comprising an agent (a'), wherein the agent comprises (a'):
  - at least one organic silicon compound (a1) from the group of silanes having one, two or three silicon atoms,
- a second container comprising an agent (a"), wherein the agent comprises (a"):
  - (a2) at least one phosphoric acid ester,
- a third container comprising an agent (a"'), said agent (a"') comprising:
  - at least 30 wt. %, based on the total weight of agent (a"'), of water; and
- a fourth container comprising an agent (b'), wherein the agent comprises (b'):
  - (b1) at least one sealant reagent comprising a film-forming polymer, and
- a fifth container comprising an agent (b"), wherein the agent comprises (b"):
  - at least one colorant compound selected from the group of pigments and/or direct dyes,
- wherein the components (a1), (a2) and (b1) have been disclosed in detail above.

In this embodiment, the ready-to-use agent (b) is prepared by mixing agents (b') and (b").

In the context of still another embodiment, preferred is a multi-component packaging unit (kit-of-parts) for dyeing keratinous material, comprising separately prepared
- a first container comprising an agent (a'), wherein the agent comprises (a'):at least one organic silicon compound (a1) from the group of silanes having one, two or three silicon atoms,
- a second container comprising an agent (a"), the agent comprising (a"):
  - (a2) at least one phosphoric acid ester,
- a third container comprising an agent (a"'), said agent comprising (a"'):
  - at least 30 wt. %, based on the total weight of agent (a"'), of water,
- a fourth container comprising an agent (b'), wherein the agent comprises (b'):

(b1) at least one sealant reagent comprising a film-forming polymer, and a fifth container comprising an agent (b"), wherein the agent comprises (b'):at least one colorant compound selected from the group of pigments and/or direct dyes, wherein the components (a1), (a2) and (b1) have been disclosed in detail above.

In this embodiment, the ready-to-use agent (b) is prepared by mixing agents (b') and (b").

Still another embodiment of the present disclosure is a multi-component packaging unit (kit-of-parts) for dyeing keratinous material, comprising separately prepared a first container comprising an agent (a'), wherein the agent comprises (a'):
(a1) at least one organic silicon compound selected from the group of silanes having one, two or three silicon atoms, a second container comprising an agent (a"), wherein the agent comprises (a"):
(a2) at least one phosphoric acid ester, at least one coloring compound selected from the group of pigments and/or direct dyes and at least 30% by weight, based on the total weight of agent (a"), of water a third container with an agent (a"') comprising at least one colorant compound selected from the group of pigments and/or direct dyes, a fourth container comprising agent (b), wherein the agent comprises (b):
(b1) at least one sealing reagent,
wherein the components (a1), (a2) and (b1) have been disclosed in detail above.

It may be preferred in this embodiment that the agent (a"') further comprises at least one phosphoric acid ester (a2).

In any embodiment of the multi-component packaging unit, it may be preferred that the agents (a"), (a"') and/or (b) further comprise a thickening agent. Particularly preferably, the agents (a"') and/or (b) further comprise a thickening agent.

Particularly preferred is a multi-component packaging unit (kit-of-parts) for dyeing keratinous material, comprising separately prepared a first container comprising an agent (a'), wherein the agent comprises (a'):
(a1) at least one organic silicon compound selected from the group of silanes having one, two or three silicon atoms, a second container comprising an agent (a"), the agent comprising (a"):
(a2) at least one phosphoric acid ester, at least 30% by weight of water, based on the total weight of the agent (a"), and optionally at least one colorant compound selected from the group of pigments and/or direct dyes, a third container comprising an agent (a"'), said agent comprising (a"'):
at least one colorant compound selected from the group of pigments and/or direct dyes, a fourth container comprising agent (b), wherein the agent comprises (b):
(b1) at least one sealing reagent.

Regarding the further preferred embodiments of the multicomponent packaging unit, the same applies mutatis mutandis as to the process.

Oligo and polymerization reactions of the organic silicon compound (a1) are already initiated when agents (a') and (a") are mixed or when agents (a'), (a") and (a"') are mixed.

It has proved to be a major challenge to optimally adjust the oligo and polymerization rate of the organic silicon compound (a1), i.e., the rate at which the silane film forms on the keratin material, to the application conditions.

When applied to human hair, for example, too fast an oligo and polymerization rate will result in polymerization being completed before all hair sections have been treated. Polymerization that is too fast makes whole-head treatment impossible. In the dyeing process, the excessively fast polymerization manifests itself in an uneven color result, so that the sections that were treated last are only poorly colored.

On the other hand, if polymerization is too slow, all areas of the keratin material can be treated without time pressure, but this increases the application time.

Surprisingly, it has been shown that the presence of a phosphoric acid ester in the agent (a) leads not only to improved elevator of the colorant compound on the keratinous material, but also to an optimal oligo and polymerization rate of the organic silicon compound (a1). This not only leads to expedient application times, but also the intensity of the coloring as well as its haptics are significantly improved.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the following steps:
applying an agent (a) to the keratinous material, wherein the agent (a) comprises:
(a1) at least one organic silicon compound selected from the group of silanes having one, two or three silicon atoms, and
(a2) at least one phosphoric acid ester,
after applying the agent (a) to the keratinous material, applying an agent (b) to the keratinous material, wherein the agent (b) comprises:
(b1) at least one sealing reagent,
wherein at least one of the agents (a) and (b) further comprises at least one colorant compound selected from the group of pigments and/or direct dyes.

2. The process according to claim 1, wherein the agent (a) comprises at least one organic silicon compound (a1) of the formula (I) and/or (II)

$$R_1R_2N\text{-}L\text{-}Si(OR_3)_a(R_4)_b \qquad (I),$$

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a stands for an integer from 1 to 3, and
b stands for the integer 3-a, and wherein in the organic silicon compound of formula (II)

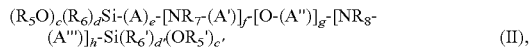

R5, R5', R5", R6, R6' and R6" independently represent a $C_1$-$C_6$ alkyl group,
A, A', A", A'" and A"" independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

C stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of the radicals e, f, g, and h is different from 0.

3. The process according to claim 1, wherein the agent (a) comprises at least one organic silicon compound (a1) of the formula (I), $$R_1R_2N\text{-}L\text{-}Si(OR_3)_a(R_4)_b \qquad (I),$$

where
$R_1$, $R_2$ both represent a hydrogen atom, and
L represents a linear, bivalent $C_1$-$C_6$-alkylene group,
$R_3$, $R_4$ independently represent a methyl group or an ethyl group,
a stands for the number 3 and
b stands for the number 0.

4. The process according to claim 2, wherein the agent (a) comprises at least one organic silicon compound (a1) of formula (I) selected from the group of
(3-Aminopropyl) triethoxysilane,
(3-Aminopropyl) trimethoxysilane,
1-(3-Aminopropyl) silantriol,
(2-Aminoethyl) triethoxysilane,
(2-Aminoethyl) trimethoxysilane,
1-(2-Aminoethyl) silantriol,
(3-Dimethylaminopropyl) triethoxysilane,
(3-Dimethylaminopropyl) trimethoxysilane,
1-(3-Dimethylaminopropyl) silantriol,
(2-Dimethylaminoethyl) triethoxysilane,
(2-dimethylaminoethyl) trimethoxysilane, and/or
1-(2-Dimethylaminoethyl) silantriol.

5. The process according to claim 2, wherein the agent (a) comprises at least one organic silicon compound (a1) of formula (II)

where
e and f both stand for the number 1,
g and h both stand for the number 0,
A and A' independently represent a linear, bivalent $C_1$-$C_6$ alkylene, and
R7 represents a hydrogen atom, a methyl group, a 2-hydroxyethyl group, a 2-alkenyl group, a 2-aminoethyl group or a group of formula (III).

6. The process according to claim 1, wherein the agent (a) comprises at least one organic silicon compound (a1) of formula (IV)

where
$R_9$ stands for a $C_1$-$C_{18}$ alkyl group,
$R_{10}$ represents a hydrogen atom or a $C_1$-$C_6$ alkyl group,
$R_{11}$ represents a $C_1$-$C_6$ alkyl group,
k is an integer from 1 to 3, and
m stands for the integer 3-k.

7. The process according to claim 6, wherein the agent (a) comprises at least one organic silicon compound (a1) of formula (IV) selected from the group of
Methyltrimethoxysilane,
Methyltriethoxysilane,
Ethyltrimethoxysilane,
Ethyltriethoxysilane,
Propyltrimethoxysilane,
Propyltriethoxysilane,
Hexyltrimethoxysilane,
Hexyltriethoxysilane,
Octyltrimethoxysilane,
Octyltriethoxysilane,
Dodecyltrimethoxysilane,
Dodecyltriethoxysilane,
Octadecyltrimethoxysilane,
Octadecyltriethoxysilane, and
Mixtures of these.

8. The process according to claim 1, wherein the agent (a) comprises at least two structurally different organic silicon compounds (a1).

9. The process of claim 1, wherein the sealing reagent comprises a compound selected from the group of film-forming polymers, alkalizing agents, acidifying agents, and mixtures thereof.

10. The process according to claim 1, wherein the agent (a) comprises, as phosphoric acid ester (a2), an ester of orthophosphoric acid with an aliphatic alcohol.

11. The process according to claim 1, wherein the agent (a) comprises, as phosphoric acid ester (a2), an ester of orthophosphoric acid with an ethoxylated aliphatic alcohol having 1 to 22 carbon atoms.

12. The process according to claim 1, wherein the agent (a) and the agent (b) each further comprise at least one colorant compound selected from the group of pigments and/or direct dyes.

13. The process according to claim 1, wherein the agent (b) further comprises a colorant compound selected from the group of pigments and/or direct dyes comprising at least one pigment selected from the group of lamellar metallic substrate platelet-based pigments, lenticular metallic substrate platelet-based pigments lenticular metallic substrate platelet, pigments based on a metallic substrate platelet comprising "vacuum metallized pigment" (VMP) at least one pigment based on natural or synthetic mica coated with at least one metal oxide and/or a metal oxychloride; and mixtures thereof.

14. The process according to claim 1, wherein the agent (a) further comprises a coloring compound selected from the group of pigments and/or direct dyes comprising at least one organic pigment selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the color index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 at least one inorganic pigment selected from the group of colored metal oxides, metal hydroxides, metal oxide hydrates, silicates, metal sulfides, complex metal cyanides, metal sulfates, bronze pigments; and and mixtures thereof; and wherein the agent (a) further comprises a coloring compound selected from the group of pigments and/or direct dyes which comprises at least one pigment selected from the group of pigments based on a lamellar metallic substrate platelet, pigments based on a lenticular metallic substrate platelet, pigments based on a metallic substrate platelet comprising "vacuum metallized pigment" (VMP) at least one pigment based on natural or synthetic mica coated with at least one metal oxide and/or a metal oxychloride; and mixtures thereof.

15. A kit-of-parts for dyeing keratinous material, comprising separately packaged
a first container including an agent (a'), wherein the agent (a') comprises:
(a1) at least one organic silicon compound selected from the group of silanes having one, two or three silicon atoms, and
a second container including an agent (a"), the agent (a") comprising:
(a2) at least one phosphoric acid ester,
a third container including an agent (b), wherein the agent (b) comprises:
(b1) at least one sealing reagent,
wherein at least one of the agents (a") and (b) further comprises at least one colorant compound selected from the group of pigments and/or direct dyes.

16. The process according to claim 1, wherein the agent (a) comprises at least one organic silicon compound (a1) of the formula (I),

where
$R_1$, $R_2$ both represent a hydrogen atom, and
L represents a propylene group ($—CH_2—CH_2—CH_2-$) or an ethylene group ($—CH_2—CH_2—$),
$R_3$, $R_4$ independently represent a methyl group or an ethyl group,
a stands for the number 3 and
b stands for the number 0.

17. The process according to claim 1, wherein the agent (a) comprises, as phosphoric acid ester (a2), an ester of orthophosphoric acid with a branched aliphatic alcohol having 11 to 14 carbon atoms.

18. The process according to claim 1, wherein the agent (a) comprises, as phosphoric acid ester (a2), Ceteth-20 phosphates.

* * * * *